United States Patent [19]

Heymes

[11] Patent Number: 5,243,043
[45] Date of Patent: * Sep. 7, 1993

[54] CEPHALOSPORINS

[75] Inventor: René Heymes, Romainville, France

[73] Assignee: Roussel Uclaf, France

[*] Notice: The portion of the term of this patent subsequent to Feb. 12, 2008 has been disclaimed.

[21] Appl. No.: 606,108

[22] Filed: Oct. 31, 1990

Related U.S. Application Data

[62] Division of Ser. No. 393,761, Jun. 30, 1982, Pat. No. 4,992,431, which is a division of Ser. No. 234,327, Feb. 13, 1981, abandoned.

Foreign Application Priority Data

Feb. 18, 1980 [FR] France .................. 80 03479

[51] Int. Cl.$^5$ .................. C07D 501/34; A61K 31/545
[52] U.S. Cl. ........................ 540/226; 540/222
[58] Field of Search .................. 540/222, 226, 225

[56] References Cited

U.S. PATENT DOCUMENTS

| | | | |
|---|---|---|---|
| 4,098,888 | 7/1978 | Ochiai et al. | 540/228 |
| 4,196,205 | 4/1980 | Heymes et al. | 540/228 |
| 4,201,779 | 5/1980 | Bormann et al. | 540/228 |
| 4,483,855 | 11/1984 | Nakav et al. | 540/228 |
| 4,973,684 | 11/1990 | Ochiai et al. | 540/226 |
| 4,992,431 | 2/1991 | Heymes et al. | 540/227 |

*Primary Examiner*—Nicholas S. Rizzo
*Attorney, Agent, or Firm*—Bierman and Muserlian

[57] ABSTRACT

Novel syn isomers of 3-alkoxymethyl or 3-alkylthio-methyl-7-[2-(2-amino-4-thiazolyl)-2-oximino-acetamido]-cephalosporanic acid compounds of the formula

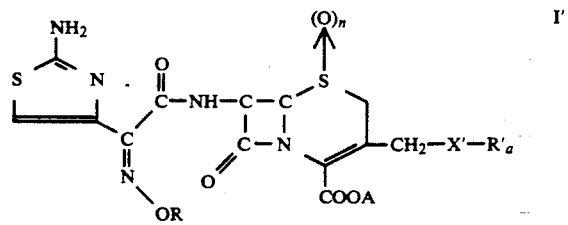

wherein R is selected from the group consisting of hydrogen, alkyl of 1 to 6 carbon atoms, alkenyl and alkynyl of 2 to 6 carbon atoms, cycloalkyl of 3 to 6 carbon atoms, acyl of an organic carboxylic acid of 1 to 18 carbon atoms and alkoxy carbonyl of 2 to 6 carbon atoms, A is selected from the group consisting of hydrogen, alkali metal, alkaline earth metal, —NH$_4$, magnesium, non-toxic, pharmaceutically acceptable organic amine and an easily cleavable ester group, Ra is selected from the group consisting of alkyl of 1 to 6 carbon atoms optionally interrupted with a heteroatom, alkenyl and alkynyl of 2 to 6 carbon atoms and optionally substituted aralkyl of 7 to 12 carbon atoms, n is 0,1 or 2, X' is selected from the group consisting of oxygen and sulfur optionally oxidized to sulfoxide or sulfone and their non-toxic, pharmaceutically acceptable acid addition salts having antibiotic activity and their preparation.

1 Claim, No Drawings

CEPHALOSPORINS

PRIOR APPLICATION

This application is a division of U.S. patent application Ser. No. 393,761 filed Jun. 30, 1982 now U.S. Pat. No. 4,992,431 which is a division of U.S. patent application Ser. No. 234,327 filed Feb. 13, 1981, now abandoned.

OBJECTS OF THE INVENTION

It is an object of the invention to provide the novel compounds of formula I' and their non-toxic, pharmaceutically acceptable acid addition salts and a novel process for their preparation.

It is another object of the invention to provide novel antibiotic compositions and to provide a novel method of combatting bacterial infections in warm-blooded animals.

These and other objects and advantages of the invention will become obvious from the following detailed description.

THE INVENTION

The novel compounds of the invention are selected from the group consisting of the syn isomers of 3-alkoxymethyl or 3-alkylthiomethyl-7-[2-(2-amino-4-thiazolyl)-2-oximino-acetamido]cephalosporanic acid compounds of the formula

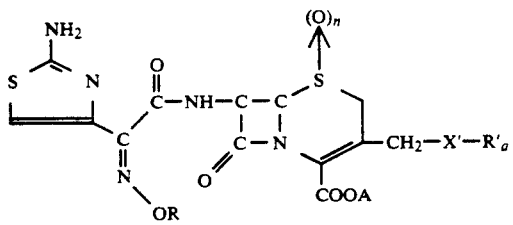

wherein R is selected from the group consisting of hydrogen, alkyl of 1 to 6 carbon atoms, alkenyl and alkynyl of 2 to 6 carbon atoms, cycloalkyl of 3 to 6 carbon atoms, acyl of an organic carboxylic acid of 1 to 18 carbon atoms and alkoxy carbonyl of 2 to 6 carbon atoms, A is selected from the group consisting of hydrogen, alkali metal, alkaline earth metal, —NH$_4$, magnesium, non-toxic, pharmaceutically acceptable organic amine and an easily cleavable ester group, Ra is selected from the group consisting of alkyl of 1 to 6 carbon atoms optionally interrupted with a heteroatom, alkenyl and alkynyl of 2 to 6 carbon atoms and optionally substituted aralkyl of 7 to 12 carbon atoms, n is 0,1 or 2, X' is selected from the group consisting of oxygen and sulfur optionally oxidized to sulfoxide or sulfone and their non-toxic, pharmaceutically acceptable acid addition salts.

Among the preferred compounds of the invention are the syn isomers of compounds of the formula

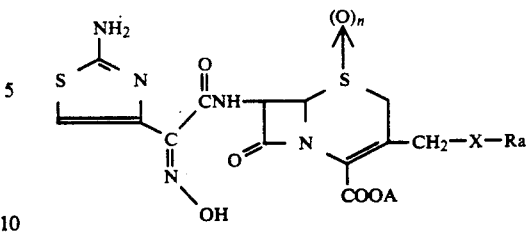

wherein A, n and R have the above definition X is selected from the group consisting of oxygen and sulfur and Ra is selected from the group consisting of alkyl of 1 to 6 carbon atoms, alkenyl and alkynyl of 2 to 6 carbon atoms and optionally substituted aralkyl of 7 to 12 carbon atoms and their non-toxic, pharmaceutically acceptable acid addition salts.

Examples of suitable groups of R are (a) alkyl of 1 to 6 carbon atoms such as methyl, ethyl, propyl, isopropyl, butyl, sec-butyl, tert.-butyl, pentyl, isopentyl, sec-pentyl, tert.-pentyl, neo-pentyl, hexyl, isohexyl, sec-hexyl and tert.-hexyl (b) alkenyl of 2 to 6 carbon atoms such as vinyl, allyl, 1-propenyl, butenyl, pentenyl and hexenyl, (c) alkynyl of 2 to 6 carbon atoms such as ethynyl, propargyl and butynyl, (d) cycloalkyl of 3 to 6 carbon atoms such as cyclopropyl, cyclobutyl, cyclopentyl and cyclohexyl and (e) acyl of an organic carboxylic acid of 1 to 18 carbon atoms such as acetyl, propionyl, butyryl, valeryl, hexanoyl, acryloyl, crotonoyl, benzyol, carbamoyl and alkoxycarbonyl such as methoxycarbonyl and ethoxycarbonyl.

The above groups a to d and certain groups of e are optionally substituted with at least one member of the group consisting of carboxyl optionally salified or esterified; alkoxycarbonyl of 2 to 6 carbon atoms such as methoxycarbonyl and ethoxycarbonyl; carbamoyl; dimethylcarbomyl; amino; dialkylamino of 1 to 6 carbon atoms such as dimethylamino and diethylamino; alkylamino of 1 to 6 carbon atoms such as methylamino; halogen such as chlorine, bromine and iodine; alkoxy of 1 to 6 carbon atoms such as methoxy, ethoxy and propoxy; alkylthio of 1 to 6 carbon atoms as methylthio and ethylthio; aryl such as phenyl; aryl heterocyclic such as tetrazolyl; arylthio such as optionally substituted phenylthio; arylheterocyclicthio such as tetrazolylthio and thiadiazolylthio optionally substituted with alkyl of 1 to 6 carbon atoms such as methyl. The groups of d) and some of e) may be substituted with alkyl as defined in a.

Examples of A are hydrogen; alkali metals such as sodium, potassium and lithium; alkaline earth metals such as calcium; magnesium; —NH$_4$; and non-toxic, pharmaceutically acceptable organic amines such as methylamine, propylamine, trimethylamine, diethylamine, triethylamine, N,N-dimethyl-ethanolamine, tris-(hydroxymethyl)-aminomethane, ethanolamine, pyridine, picoline, dicyclohexylamine, morpholine, benzylamine, procaine, lysine, arginine, histidine and N-methylglucamine.

Examples of A as an easily cleavable esters are methoxymethyl, ethoxymethyl, isopropoxymethyl, α-methoxyethyl, α-ethoxyethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert.-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert.-butylcarbonyloxyethyl, 1-acetyloxypropyl, 1-hexadecanoyloxyethyl, 1-propionyloxypropyl, 1-methoxycarbonyloxyethyl, methoxycarbonyloxymethyl, 1-acetyloxybutyl, 1-acetyloxyhexyl, 1-acetyloxyheptyl, phthalidyl, 5,6-dimethoxyphthalidyl, tert.-butylcarbonylmethyl, allyl, 2-chloroallyl, methoxycarbonylmethyl, benzyl and tert.-butyl.

Other easily cleavable ester groups for A are methoxyethoxymethyl, dimethylaminoethyl, cyanomethyl, tert.-butyloxycarbonylmethyl, 2,2-ethylenedioxyethyl, cyanoethyl, 2,2-dimethoxyethyl, 2-chloroethoxymethyl, 2-hydroxyethoxyethyl, 2,3-epoxypropyl, 3-dimethylamino-2-hydroxypropyl, 2-hydroxyethyl, 2-methylamino-ethoxymethyl, 2-aminoethoxymethyl, 3-methoxy-2,4-thiadiazol-5-yl, 2-tetrahydropyranyl, 2-methoxyprop-2-yl, 1-hydroxyprop-2-yl, isopropyl, carbamoylmethyl, chloromethyl, 2-chloroethyl, acetylmethyl, 2-methylthioethyl and thiocyanatomethyl.

Still further easily cleavable ester groups for A are 2-chloro-1-acetyloxyethyl, 2-bromo-1-acetyloxyethyl, 2-fluoro-1-acetyloxyethyl, 2-methoxy-1-acetyloxyethyl, 2-methyl-1-acetyloxypropyl, 2-acetyloxyprop-2-yl, 1-methoxyacetyloxyethyl, 1-acetylcarbonyloxyethyl, 1-hydroxyacetyloxyethyl, 1-formylcarbonyloxyethyl, 1-(2-thienyl)-carbonyloxyethyl, 1-(2-furyl)-carbonyloxyethyl, 1-(5-nitro-2-furyl)-carbonyloxyethyl, 1-(2-pyrrolyl)-carbonyloxyethyl, 1-(propionyloxycarbonyloxyethyl), 1-(propyloxycarbonyloxy)-ethyl, 1-(isopropyloxycarbonyloxy)-ethyl, 1-(methoxyethoxycarbonyloxy)-ethyl, 1-(allyloxycarbonyloxy)-ethyl, 1-(2,3-epoxy)-propyloxycarbonyloxyethyl, 1-(2-furyl)-methoxycarbonyloxyethyl, 1-(2-fluoro)-ethoxycarbonyloxyethyl, 1-(methoxycarbonyloxy)-propyl, 2-(methoxycarbonyloxy)-prop-2-yl, (methoxycarbonyloxy)-chloromethyl, 1-(methoxycarbonyloxy)-2-chloro-ethyl, 1-(methoxycarbonyloxy)-2-methoxy-ethyl and 1-(methoxycarbonyloxy)-1-allyl.

Examples of Ra are the substituents a, b and c of the definition of R above and especially preferred are methyl, ethyl, propyl, isopropyl, allyl, methoxymethyl and ethoxymethyl. Among the preferred aralkyl groups of Ra are benzyl and phenylethyl optionally substituted with at least one member of the group consisting of carboxy, amino, aminoalkyl of 1 to 6 carbon atoms, alkyl of 1 to 6 carbon atoms, dialkylamino of 1 to 6 carbon atoms and dialkylaminoalkyl of 1 to 6 carbon atoms such as dimethylaminoethyl.

The compounds of formula I' have a free amino group which can be salified with a non-toxic, pharmaceutically acceptable acid such as mineral acids like phosphoric acid, sulfuric acid, hydrochloric acid and hydrobromic acid and organic acids such as acetic acid, trifluoroacetic acid, maleic acid, tartaric acid, citric acid, methanesulfonic acid, benzenesulfonic acid and p-toluene sulfonic acid.

Among the preferred compounds of formula I are those wherein R is selected from the group consisting of hydrogen and alkyl of 1 to 4 carbon atoms optionally substituted with amino or carbonyl free salified or esterified and those wherein Ra is alkyl of 1 to 6 carbon atoms and the compounds of formula I wherein Ra is methyl and n is 0.

Another preferred group of compounds of the invention ion are syn isomers of compounds of the formula

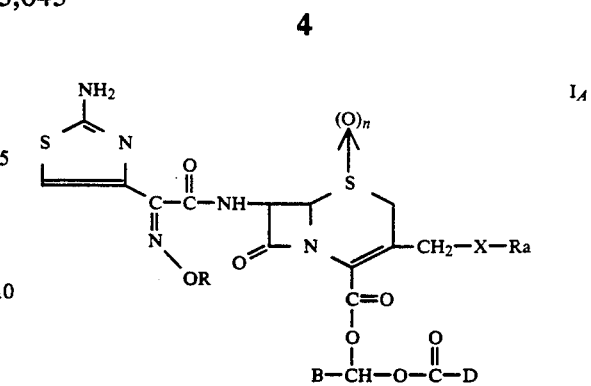

wherein R, n, X and Ra have the above definitions, B is selected from the group consisting of hydrogen and optionally subsituted alkyl of 1 to 5 carbon atoms and D is selected from the group consisting of optionally substituted alkyl and alkoxy of 1 to 15 carbon atoms, especially 1 to 5 carbon atoms and their non-toxic, pharmaceutically acceptable acid addition salts.

Among the preferred compounds of formula $I_A$ are those wherein B is hydrogen, methyl or ethyl and those wherein D is methyl, ethyl, methoxy or ethoxy.

Specific preferred compounds of the invention are the syn isomer of 3-methoxymethyl-7-[2-(2-amino-4-thiazolyl)-2-hydroxyimino-acetamido]-ceph-3-eme-4-carboxylic acid, the syn isomer of 3-methoxymethyl-7-[2-(2-amino-4-thiazolyl)-2-methoxyimino-acetamido]-ceph-3-eme-4-carboxylic acid, the syn isomer of 3-methylthiomethyl-7-[2-(2-amino-4-thiazolyl)-2-hydroxyimino-acetamido]-ceph-3-eme-4-carboxylic acid, the syn isomer of 3-methylthiomethyl-7-[2-(2-amino-4-thiazolyl)-2-methoxyimino-acetamido]-ceph-3-eme-4-carboxylic acid and the syn isomer of 3-ethoxymethyl-7-[2-(2-amino-4-thiazolyl)-2-hydroxy-imino-acetamido]-ceph-3-eme-4-carboxylic acid and their salts with alkali metals, alkaline earth metals, magnesium, ammonia and non-toxic, pharmaceutically acceptable organic amines and their easily cleavable esters, 1-acetyloxyethyl 3-methylthiomethyl-7-[2-(2-amino-4-thiazolyl)-2-hydroxyimino-acetamido]-ceph-3-eme-4-carboxylate, 1-acetyloxyethyl 3-methoxymethyl-7-[2-(2-amino-4-thiazolyl)-2-hydroxyiminoacetamido]-ceph-3-eme-4-carboxylic acid and 1-acetyloxyethyl 3-ethoxymethyl-7-[2-(2-amino-4-thiazolyl)-2-hydroxyimino-acetamido]-ceph-3-eme-4-carboxylate.

The compounds of formula I' may exist in the indicated form or in the form of the formula

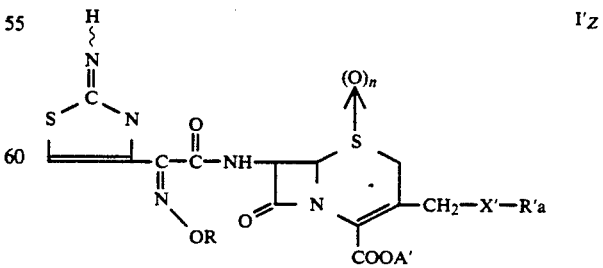

The novel process of the invention for the preparation of compounds of formula I' comprises either (A) reacting a compound of the formula

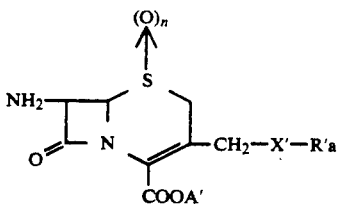

wherein Ra, X' and n have the above definitions and A' is selected from the group consisting of hydrogen and an easily eliminable ester group with a syn isomer of a compound of the formula

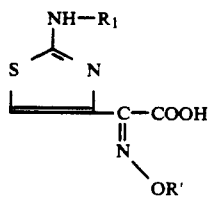

or a functional derivative of the acid wherein $R^1$ is selected from the group consisting of hydrogen and an amino protective group and R' is selected from the group consisting of hydrogen, a hydroxy protective group, alkyl of 1 to 6 carbon atoms, alkenyl and alkynyl of 2 to 6 carbon atoms, cycloalkyl of 3 to 6 carbon atoms and acyl alkoxycarbonyl of 1 to 18 carbon atoms, all the said groups being optionally substituted to obtain a compound of the formula

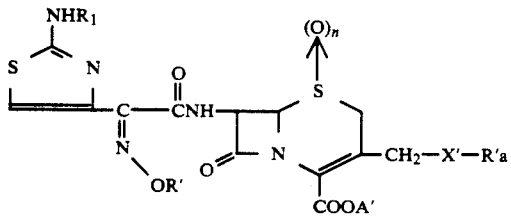

wherein $R_1$, R', A', Ra, X' and n have the above definitions or (B) reacting a compound of the formula

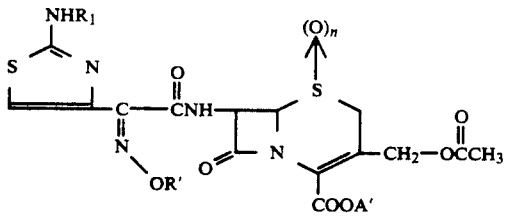

wherein $R_1$, R', A' and n have the above definitions with either a compound of the formula Ra-SH wherein Ra has the above definition or with 2-mercaptopyridine-N-oxide and then with a compound of the formula Ra'OH to obtain the corresponding compound of formula IV and optionally when n is 0 and X' is sulfur or oxygen, treating the compound of formula IV with an oxidation agent to obtain a compound of formula IV wherein n is 1 or 2 and X' is oxygen, sulfur or sulfur in the form of sulfoxide or sulfone and if desired, the compounds of formula IV may be subjected to one or more of the following reactions in any order (a) cleaving the ester groups or the amino protective groups or the hydroxyl protective groups by hydrolysis, hydrogenolysis or reaction with thiourea, (b) esterification or salification with a base of the carboxylic group or groups (c) salification with an acid of the amino group or groups.

Examples of easily eliminable ester groups of A' are butyl, isobutyl, tert.-butyl, pentyl, hexyl, acetoxymethyl, propionyloxymethyl, butyryloxymethyl, valeryloxymethyl, pivaloyloxymethyl, 2-acetoxyethyl, 2-propionyloxyethyl, 2-butyryloxyethyl, 2-iodoethyl, β,β,β-trichloroethyl, vinyl, allyl, ethynyl, propynyl, benzyl, 4-methoxybenzyl, 4-nitrobenzyl, phenethyl, trityl, diphenylmethyl, 3,4-dimethoxyphenyl, phenyl, 4-chlorophenyl, tolyl and tert.-butylphenyl.

Examples of amino protective groups of $R_1$ are alkyl of 1 to 6 carbon atoms, especially tert.-butyl and tert.-amyl and aliphatic, aromatic and heterocyclic acyl groups and a carbamoyl group. Examples of acyl groups of suitable lower alkanoic acids are formyl, acetyl, propionyl, butyryl, isobutyryl, valeryl, isovaleryl, oxalyl, succinyl and pivaloyl. The acyl groups may be substituted with chlorine, bromine, iodine or fluorine such as chloroacetyl, dichloroacetyl, trichloroacetyl, bromoacetyl and trifluoroacetyl, $R_1$ may also be lower alkoxy carbonyl or cycloalkoxycarbonyl such as methoxycarbonyl, ethoxycarbonyl, propoxycarbonyl, 1-cyclopropyl-ethoxycarbonyl, isopropoxycarbonyl, butyloxycarbonyl, tert.-butyloxycarbonyl, pentyloxycarbonyl and hexyloxycarbonyl or acyl of an aryl carboxylic acid such as benzoyl, toluolyl, naphthoyl, phthaloyl, mesyl, phenylacetyl and phenylpropionyl or an aralkoxycarbonyl group such as benzyloxycarbonyl.

$R_1$ may also be araloweralkyl such as benzyl, 4-methoxybenzyl, phenethyl, trityl, 3,4-dimethoxybenzyl or benzhydryl; a haloalkyl such as trichloroethyl; chlorobenzoyl, p-nitrobenzoyl, p-tert.-butylbenzoyl, phenoxyacetyl, caprylyl, n-decanoyl, acryloyl, trichloroethoxycarbonyl, methylcarbamoyl, phenylcarbamoyl, naphthylcarbamoyl and the corresponding thio carbamoyl groups. The list is not intended to be limiting and may include other amine protecting groups such as the groups known in the peptide chemistry.

The hydroxy protecting groups of R' may be acyl of an organic carboxylic acid such as formyl, acetyl, chloroacetyl, bromoacetyl, dichloroacetyl, trichloroacetyl, trifluoroacetyl, methoxyacetyl, phenoxyacetyl, benzoyl, benzoylformyl and p-nitrobenzoyl as well as ethoxycarbonyl, methoxycarbonyl, propoxycarbonyl, β,β,β-trichloroethoxycarbonyl, benzyloxycarbonyl, tert.-butoxycarbonyl, 1-cyclopropylethoxycarbonyl, tetrahydropyranyl, tetrahydrothiopyranyl, methoxytetrahydropyranyl, trityl, benzyl, 4-methoxy-benzyl, benzyhydryl, trichloroethyl, 1-methyl-1-methoxyethyl, phthaloyl; acyls such as propionyl, butyryl, isobutylryl, valeryl, isovaleryl, oxalyl, succinyl, pivaloyl, phenylacetyl, phenylpropionyl, mesyl, chlorobenzoyl, p-nitrobenzoyl, p-tert.-butylbenzoyl, caprylyl, acryloyl, methylcarbamoyl, phenylcarbamoyl and naphthylcarbamoyl.

In the preferred mode of the process of the invention, the compound of formula II is reacted with a functional derivative of the acid of formula III such as the acid halide, symetric or mixed acid anhydride, amine, azide or active ester. Examples of mixed acid anhydride is that formed with isobutyl chloroformate or with pivaloyl chloride and mixed carboxylic acid-sulfonic acid anhydrides such as formed with p-toluene sulfonyl chloride. The anhydride may be formed in situ by reaction with an N,N-disubstituted carbodiimide such as N,N-dicyclohexylcarbodiimide. Example of an active ester is that formed with 2,4-dinitrophenol or hydroxybenzothiazole and the acid halide may be the acid chloride or acid bromide, for example.

The acylation reaction is preferably effected in an organic solvent such as methylene chloride but other solvents such as tetrahydrofuran, chloroform or dimethylformamide may also be used. When the acid halide is used and generally when a molecule of hydrogen halide is freed during the reaction, the reaction is preferably effected in the presence of a base such as sodium hydroxide, potassium hydroxide, sodium acetate, triethylamine, pyridine, morpholine or N-methylmorpholine. The acylation is usually effected at temperatures equal to or less than room temperature and the preferred mixed anhydride is a carboxylic acid-sulfonic acid anhydride.

The reaction of a compound of the formula Ra'SH with a compound of formula V is preferably effected under the conditions of French Patent No. 2,379,540 operating in the presence of the etherate of boron trifluoride in acetic acid or nitro-methane.

The reaction of the compound of formula V with 2-mercapto-pyridine N-oxide and then the RaOH alcohol is preferably effected under the conditions of French Patent No. 2,119,074. The ether formation is preferably effected in the presence of a copper salt such as cupric chloride.

The oxidation of the compounds of formula IV is preferably effected with a peracid such as peracetic acid, perphthalic acid, m-chloroperbenzoic acid or perbenzoic acid or hydrogen peroxide.

Depending on the values of $R_1$, $R'$ and $A'$, the compounds of formula IV may or may not fall within the scope of formula I. When $R_1$ is hydrogen, $R'$ is not a hydroxyl protective group which can be eliminated and $A'$ is not easily cleavable ester group, the compounds of formula IV fall within the scope of formula I. In the other cases, the compounds of formula IV may be reacted with one or more of hydrolysis agents, hydrogenolysis agents or thiourea to eliminate $R_1$ when it is an amino protective group, to remove $R'$ when it is different from R and/or to eliminate $A'$ when it is an easily cleavable ester group.

However, it is also possible to eliminate the $R_1$ group without touching the $R'$ and $A'$ substitutents when these are desired to be conserved for example when $A'$ is an ester group which is desired to be conserved such as propionyloxymethyl. The nature of the reactants put in play in such a case are well known to one skilled in the art and examples of such reactions are shown in the examples below.

A non-exhaustive enumeration of the ways to eliminate the different groups follows. The removal of $R_1$ may be effected by acidic or basic hydrolysis or by the use of hydrazine. Acid hydrolysis is preferred to eliminate optionally substituted alkoxy and cycloalkoxycarbonyl groups such as tert.-pentyloxycarbonyl, or tert.-butyloxycarbonyl; optionally substituted or alkoxycarbonyl groups such as benzyloxycarbonyl; trityl; benzhydryl; tert.-butyl; or 4-methoxybenzyl. The preferred acids for the hydrolysis are hydrochloric acid, benzene sulfonic acid, p-toluene sulfonic acid, formic acid or trifluoroacetic acid but other mineral or organic acids may also be used.

The basic hydrolysis is preferably used to remove acyl groups such as trifluoroacetyl and the base is preferably an inorganic base such as sodium hydroxide or potassium hydroxide. Equally useful bases are magnesium hydroxide, baryta or alkali metal carbonates or bicarbonates such as sodium carbonate, sodium bicarbonate, potassium carbonate or potassium bicarbonate or other bases. Also useful are sodium acetate and potassium acetate. The hydrolysis using hydrazine is preferably used to remove groups such as phthaloyl.

The $R_1$ group may also be removed with a zinc-acetic acid system for groups such as trichloroethyl and groups such as benzyhydryl and benzyloxycarbonyl are preferably removed with hydrogen in the presence of a catalyst. The chloroacetyl group is preferably removed by action of thiourea in an acid or neutral media by the reaction described in Masaki, J.A.C.S., Vol. 90 (1968), p. 4508. Other methods known in the literature for the removal of protective groups are equally useful.

Among the preferred groups are formyl, acetyl, ethoxycarbonyl, mesyl, trifluoroacetyl, chloroacetyl and trityl and the preferred acid used is trifluoroacetic acid.

The removal of $A'$ or $R'$ groups, when it is necessary, is realized under similar conditions for those for the removal of $R_1$ groups. Among others, one may use acid hydrolysis to remove optionally substituted alkyl or aralkyl groups and the acid is preferably selected for the group consisting of hydrochloric acid, formic acid, trifluoroacetic acid and p-toluene sulfonic acid. The other groups of $A'$ or $R'$ may, when desired, be removed by procedures known to one skilled in the art, preferably under moderate conditions such as at room temperature or slight heating.

Naturally when for example $R_1$ and $A'$ or $R'$ are removable by different types of reactions, the compounds of formula IV can be subjected to different agents of the types discussed above.

The salification of the products is effected by the usual methods. For example, a product in the form of an acid or a solvate such as in ethanol solvate or an acid hydrate is reacted with a mineral base such as sodium hydroxide, potassium hydroxide, sodium carbonate, sodium bicarbonate, potassium carbonate or potassium bicarbonate. Equally useful are salts of mineral acids such as trisodium phosphate and salts of organic acids.

Examples of salts of organic acids are the sodium salts of optionally unsaturated aliphatic carboxylic acids of 1 to 18 carbon atoms, preferably 2 to 10 carbon atoms. The aliphatic chain may be interrupted with one or more heteroatoms such as oxygen or sulfur or substituted with aryl such as phenyl, thienyl or furyl or with one or more hydroxy or one or more halogens such as fluorine, chlorine or bromine and preferably chlorine or one more carboxylic or lower alkoxycarbonyl group, preferably methoxycarbonyl, ethoxycarbonyl and propoxycarbonyl or one or more aryloxy such as phenoxy. When organic acids are used, sufficiently soluble aromatic acids such as substituted benzoic acid, preferably with lower alkyl substituents, are preferably used.

Examples of specific organic acids whose sodium salts are used are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic, glutaric acid, monoethyl adipate, hexanoic acids, heptanoic acids, decanoic acids, oleic acid, stearic acid, palmitic acid, 3-hydroxy-propionic acid, 3-methoxy-propionic acid, 3-methylthio-butyric acid, 4-chloro-butyric acid, 4-phenyl-butyric acid, 3-phenoxy-butyric acid, 4-ethyl-benzoic acid and 1-propyl-benzoic acid. The preferred sodium salts are sodium acetate, sodium 2-ethylhexanoate and sodium diethylacetate.

The salification may also be effected with an organic base such as triethylamine, diethylamine, trimethylamine, propylamine, N,N-dimethylethanolamine, tris-(hydroxymethyl)-aminomethane, methylamine, ethanolamine, pyridine, picoline, dicyclohexylamine, morpholine and benzylamine. Also useful for the salification are arginine, lysine, procaine, histidine and N-methylglucamine.

The salification is preferably effected in a solvent or a mixture of solvents such as water, ether, methanol, ethanol or acetone. The salts may be crystalline or amorphous depending upon the reaction conditions. Crystalline salts are preferably obtained by reacting the free acid with a salt of an aliphatic carboxylic acid, preferably sodium acetate. The salification with organic or mineral acids may be effected under the usual conditions.

The eventual esterification of the products may be effected under classical conditions, generally reacting an acid of formula I or a functional derivative thereof with a compound of formula Z-Re wherein Z is —OH or a halogen such as chlorine, bromine or iodine and Re is the ester group to be introduced which has been non-exhaustively discussed. In certain cases, it is advantageous to effect esterification with a product containing an amino and/or oxyimino group optionally blocked with a protective group for the amine and oxyimino group.

In a preferred mode of the prcess of the invention for the preparation of compounds of formula I', a compound of formula III wherein R<sub>1</sub> is a protective amino group in the form of a mixed anhydride with a sulfonic acid is used. Preferably, the sulfonic acid group is p-toluene sulfonic acid and R<sub>1</sub> is trityl.

In another mode of a process for the preparation of a compound of formula I', a compound of the formula

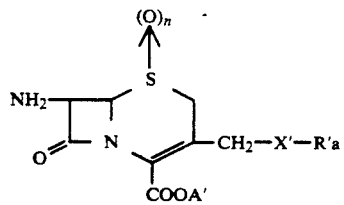

wherein Ra, A' and n and X' have the above definitions is reacted with the syn isomer of a compound of the formula

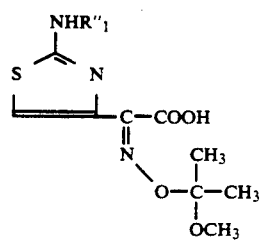

or a functional derivative of the acid wherein R<sub>1</sub>″ is an amine protective group to obtain a compound of the formula

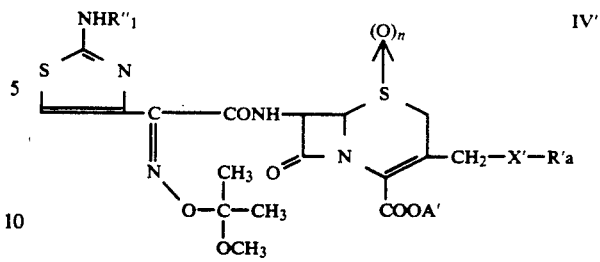

in which A', R″<sub>1</sub>, Ra, X' and a have the above meaning, which product of formula (IV') is treated with an acid under moderate conditions, to obtain a product of formula (VI):

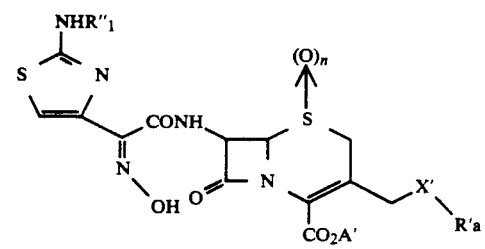

which may, if desired, be esterified or salified and reacting the latter in the presence of a base with a compound of the formula Rd—Hal wherein Hal is a halogen and Rd is selected from the group consisting of alkyl of 1 to 6 carbon atoms, alkenyl and alkynyl of 2 to 6 carbon atoms, cycloalkyl of 3 to 6 carbon atoms, acyl and alkoxycarbonyl, all optionally substituted to obtain a compound of the formula

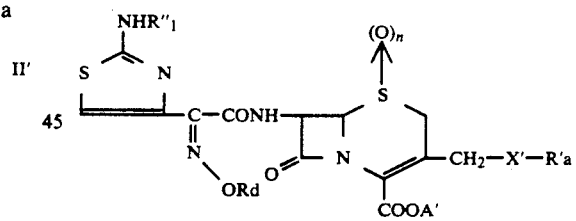

and subjecting the compounds of formulae VI or VII to hydrolysis, hydrogenolysis or action of thiourea to remove R<sub>1</sub>″ and, if desired, or necessary, subjecting the product to one or more of the following reactions in any order (a) removal of ester group or groups, (b) esterification or salification with a base the carboxyl group or groups and (c) salification of the amino group or groups with an acid.

The R<sub>1</sub>″ protective amino group may be any one of the R<sub>1</sub> groups discussed above and the functional derivatives of the acid of formula III' may be those discussed for the compounds of formula III. The acid used to treat the compound of formula IV' is preferably aqueous hydrochloric acid. The base used with Rd-Hal is preferably triethylamine or pyridine. The treatment of the compounds of formulae VI and VII is effected under the conditions described for the compounds of formula IV.

The antibiotic compositions of the invention are comprised of an antibiotically effect amount of at least one compound of formula I' and their non-toxic, pharmaceutically acceptable acid addition salts and an inert pharmaceutical carrier. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers. These compositions can, especially, be presented in the form of a powder intended to be dissolved extemporaneously in an appropriate vehicle, for example apyrogenetic sterile water. The compositions on the invention possess very good antibiotic activity against gram positive bacteria such as staphylocoecus, streptococcus, particularly penicillin resistant staphylococcus as well as against gram negative bacteria such as colliform bacteria. Klebsiella Salmonella, Proteus and Pseudomonas.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegomons, eresipels, acute primitive or post-grip staphylococcia, bronchopneumonia or pulmonary suppurations. They are equally useful for the treatment of collibacillosis and associated infections, infections of Proteus, Klebsiella, Salmonella, Pseudomonas and other infections caused by gram negative bacteria. The compositions are also useful to disinfect surgical instruments.

Among the preferred compositions of the invention are those of formula 1 wherein R is hydrogen or alkyl of 1 to carbon atoms optionally substituted with free, esterified. or salified carboxyl or —NH₂, those wherein $R_a$ is alkyl of 1 to 6 carbon atoms, especially methyl, those wherein n is 0 and their non-toxic, pharmaceutically acceptable acid addition salts.

Also prefered compositions are those containing the syn isomers of compounds of the formula

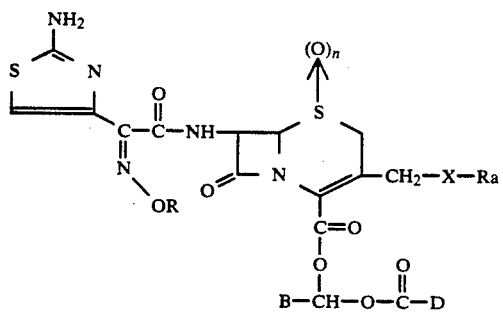

wherein R, n, X and Ra have the above definitions, B is selected from the group consisting of hydrogen and optionally substituted alkyl or 1 to 5 carbon atoms and D is selected from the group consisting of optionally substituted alkyl and alkoxy of 1 to 15 carbon atoms, especially 1 to 5 carbon atoms and their non-toxic, pharmaceutically acceptable acid addition salts.

Among the preferred compounds of formula $I_A$ are those wherein B is hydrogen, methyl or ethyl and those wherein D is methyl, ethyl, methoxy and ethoxy.

The most preferred antibiotic compositions of the invention are those wherein the active compound is selected from the group consisting of the syn isomers of 3-methoxymethyl -7-[2-(2-amino-4-thiazolyl)-2-hydroxyimino-acetamido]-ceph- 3-eme-4-carboxylic acid, the syn isomer of 3-methoxymethyl-7-[2-(2-amino-4-thiazolyl)-2-methoxyimine-acetamide]-ceph-3-eme-4-carboxylic acid, the syn isomer of 3-methylthiomethyl-7-[2-(2-amino-4-thiazolyl)-2-hydroxyimino-acetamido]-ceph -3-eme-4-carboxylic acid, the syn isomer of 3-methylthiomethyl-7-[2(2-amino-4-thiazolyl)-2-methoxyimino-acetamide]-ceph-3-eme-4-carboxylic acid and the syn isomer of 3-ethoxymethyl-7[2(2-amino-4-thiazolyl)-2-hydroxyimino-acetamido]-ceph-3-eme-4-carboxylic acid and their salts with alkali metals, alkaline earth metals, magnesium, ammonia and non-toxic, pharmaceutically acceptable organic amines and their easily cleavable esters, 1-acetyloxyethyl 3-methylthiomethyl-7-[2(2-amino-4-thiazolyl)-2-hydroxyiminoacetamide]-ceph-3-eme-4-carboxylate, 1-acetyloxyethyl 3-methoxymethyl-7-[2(2-amino-4-thiazolyl)-2-hydroxyimino -acetamido]-ceph-3-eme-4-carboxylate and 1-acetyloxyethyl 3-ethoxymethyl-7-[2-(2-amino-4-thiazolyl)-2-hydroxyimino-acetamido]-ceph-3-eme-4-carboxylate.

The novel method of the invention of combating bacterial infectious in warm-blooded animals, including humans comprises administering to warm-blooded animals an antibacterially effective amount of at least one compound of formula I' and their non-toxic, pharmaceutically acceptable acid addition salts. The compounds may be administered orally, rectally, parenterally, especially intramuscularly, and applied topically to the skin or mucous. The compounds of formula ($I_A$), more particularly the esters of 1-methoxycarbonyloxyethyl or 1-acetyloxyethyl may especially be administered orally. The daily active dose will depend upon the compound used, the condition being treated and the method of administration but the usual daily dose when administered orally is 5 to 80 mg/kg or when administered intramuscularly is 10 to 20 mg/kg in three times.

The novel intermediate products of the invention are the syn isomers of compounds of the formula

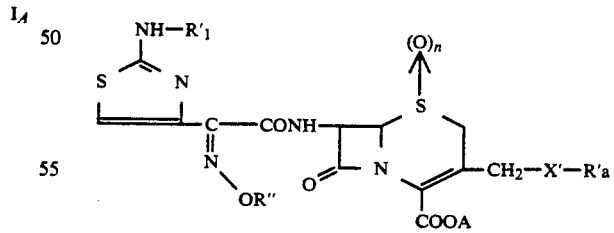

wherein X', Ra, n and A have the above definitions and either $R_1'$ is a amino protective group and R" has the definition of R' or $R_1'$ is hydrogen and R" is a hydroxyl protective group. Particularly preferred are the compounds of formula IV' and VI.

In addition to the compounds exemplified in the following working examples, examples of suitable compounds of formula I' are illustrated in the following Table which indicates the values of n, X', Ra, A and R

TABLE

| n | X' | R'a | A | R |
|---|----|-----|---|---|
| 0 | O | CH$_3$ | H | —CH$_2$—CH$_3$ |
| 0 | O | CH$_3$ | H | —CH(CH$_3$)$_2$ |
| 0 | O | CH$_3$ | H | —CH=CH$_2$ |
| 0 | O | CH$_3$ | —CH$_2$—OC(=O)C$_2$H$_5$ | —CH$_2$—CH$_3$ |
| 0 | O | CH$_3$ | —CH$_2$—OC(=O)C$_2$H$_5$ | —CH(CH$_3$)$_2$ |
| 0 | O | CH$_3$ | —CH$_2$—OC(=O)C$_2$H$_5$ | —CH=CH$_2$ |
| 0 | O | CH$_3$ | —CH(CH$_3$)—OC(=O)CH$_3$ | —CH$_3$ |
| 0 | O | CH$_3$ | H | —CH$_2$—C(=O)—O—C$_6$H$_5$ |
| 0 | O | CH$_3$ | CH$_2$—OC(=O)—C(CH$_3$)$_3$ | —CH$_3$ |
| 0 | O | CH$_3$ | —CH(CH$_3$)—OC(=O)CH$_3$ | —CH=CH$_2$ |
| 0 | O | CH$_3$ | H | —CH$_2$—CO$_2$H |
| 0 | O | CH$_3$ | H | —C(CH$_3$)$_2$CO$_2$H |
| 0 | O | CH$_3$ | H | —(CH$_2$)$_2$NH$_2$ |
| 0 | O | CH$_3$ | H | —CO—C$_6$H$_5$ |
| 0 | O | CH$_3$ | H | —COCH$_3$ |
| 0 | O | CH$_3$ | H | —CO$_2$CH$_2$CH$_3$ |
| 0 | O | CH$_3$ | H | —CON(CH$_3$)$_2$ |
| 0 | O | —CH$_2$—CH$_3$ | H | —CH$_2$—CO$_2$H |
| 0 | O | —CH$_2$—CH$_3$ | H | —C(CH$_3$)$_2$—CO$_2$H |
| 0 | O | —CH$_2$—CH$_3$ | H | —(CH$_2$)$_2$NH$_2$ |
| 0 | O | —CH$_2$—CH$_3$ | —CH$_2$OC(=O)—C$_2$H$_5$ | H |
| 0 | O | —CH$_2$—CH$_3$ | —CH$_2$OC(=O)—C$_2$H$_5$ | CH$_3$ |
| 0 | O | —CH$_2$—CH$_3$ | —CH$_2$OC(=O)—C(CH$_3$)$_3$ | H |
| 0 | O | —CH$_2$—CH$_3$ | —CH$_2$OC(=O)—C(CH$_3$)$_3$ | CH$_3$ |
| 0 | O | —CH$_2$—CH$_3$ | —CH(CH$_3$)—OC(=O)CH$_3$ | H |
| 0 | O | —CH$_2$—CH$_3$ | —CH(CH$_3$)—OC(=O)CH$_3$ | CH$_3$ |
| 0 | S | —CH$_3$ | H | —CH$_2$CH$_3$ |
| 0 | S | —CH$_3$ | H | —CH$_2$—CH$_3$ |
| 0 | S | —CH$_3$ | H | —CH—(CH$_3$)$_2$ |

TABLE-continued

| n | X' | R'a | A | R |
|---|----|----|---|---|
| 0 | S | $-CH_3$ | $CH_2O\underset{O}{\overset{\|}{C}}-C_2H_5$ | $-CH_2-CH_3$ |
| 0 | S | $-CH_3$ | $CH_2O\underset{O}{\overset{\|}{C}}-C_2H_5$ | $-CH(CH_3)_2$ |
| 0 | S | $-CH_3$ | $CH_2O\underset{O}{\overset{\|}{C}}-C_2H_5$ | $-CH=CH_2$ |
| 0 | S | $-CH_3$ | $\underset{CH_3}{\overset{\|}{CH}}-O\underset{O}{\overset{\|}{C}}CH_3$ | $-CH_3$ |
| 0 | S | $-CH_3$ | $CH_2-O\underset{O}{\overset{\|}{C}}-C(CH_3)_3$ | $-CH_3$ |
| 0 | S | $-CH_3$ | $-\underset{CH_3}{\overset{\|}{CH}}-O\underset{O}{\overset{\|}{C}}CH_3$ | $-CH=CH_2$ |
| 0 | S | $-CH_3$ | H | $-C(CH_3)_2CO_2H$ |
| 0 | S | $-CH_3$ | H | $-(CH_2)_2NH_2$ |
| 0 | S | $-CH_3$ | H | $-CO-\phi$ |
| 0 | S | $-CH_3$ | H | $-COCH_3$ |
| 0 | S | $-CH_3$ | H | $-CON(CH_3)_2$ |
| 0 | S | $-CH_2CH_3$ | H | $-CH_3$ |
| 0 | S | $-CH_3-CH_3$ | H | $-CH_2-CO_2H$ |
| 0 | S | $-CH_2-CH_3$ | H | $-C(CH_3)_2CO_2H$ |
| 0 | S | $-CH_2-CH_3$ | H | $-(CH_2)_2NH_2$ |
| 0 | S | $-CH_2-CH_3$ | $-CH_2-O\underset{O}{\overset{\|}{C}}C_2H_5$ | H |
| 0 | S | $-CH_2-CH_3$ | $-CH_2-O\underset{O}{\overset{\|}{C}}C_2H_5$ | $-CH_3$ |
| 0 | S | $-CH_3$ | H | $-CH_2-\underset{O}{\overset{\|}{C}}-\phi$ |
| 0 | S | $-CH_3$ | $-CH_2-O\underset{O}{\overset{\|}{C}}-CH_2-\phi$ | H |
| 0 | S | $-CH_2-CH_3$ | $-CH_2-O\underset{O}{\overset{\|}{C}}-C(CH_3)_3$ | H |
| 0 | S | $-CH_2-CH_3$ | $-CH_2-O\underset{O}{\overset{\|}{C}}-C(CH_3)_3$ | $-CH_3$ |
| 0 | S | $-CH_2-CH_3$ | $-\underset{CH_3}{\overset{\|}{CH}}-O\underset{O}{\overset{\|}{C}}-CH_3$ | H |
| 0 | S | $-CH_2-CH_3$ | $-\underset{CH_3}{\overset{\|}{CH}}-O\underset{O}{\overset{\|}{C}}CH_3$ | $-CH_3$ |
| 0 | O | $-CH(CH_3)_2$ | H | H |
| 1 | O | $-CH_3$ | H | H |
| 1 | O | $-CH_3$ | H | $-CH_3$ |

TABLE-continued

| n | X' | R'a | A | R |
|---|----|-----|---|---|
| 0 | O | —CH₃ | H | ▽—CO₂H |
| 0 | O | —CH₃ | H | —CH(CH₃)—CO₂H |
| 0 | O | —(CH₂)₂CH₃ | H | H |
| 0 | O | —CH₂—CH=CH₂ | H | H |
| 0 | O | —CH₂—C₆H₅ | H | H |
| 0 | S | —CH(CH₃)₂ | H | H |
| 0 | S | —CH(CH₃)₂ | H | —CH₃ |
| 1 | S | —CH₃ | H | H |
| 1 | S | —CH₃ | H | —CH₃ |
| 0 | S | —CH₃ | H | ▽—CO₂H |
| 0 | S | —CH₃ | H | —CH(CH₃)—CO₂H |
| 0 | S | —(CH₂)₂CH₃ | H | H |
| 0 | S | —(CH₂)₂CH₃ | H | —CH₃ |
| 0 | S | —CH₂—CH=CH₂ | H | —CH₃ |
| 0 | S | —CH₂—C₆H₅ | H | —CH₃ |
| 0 | S | —CH₂—CH=CH₂ | H | H |
| 0 | S | —CH₂—C₆H₅ | H | H |

The starting compounds of formula II are known or can be made by the processes described in French Patent Nos. 2,379,540 and 2,119,074. The compounds of formulae III and V are described, for example, in French Patent Nos. 2,346,014 and 2,385,722.

In the following examples there are several preferred embodiments to illustrate the invention but it should be understood that the invention is not intended to be limited to the specific embodiments.

EXAMPLE 1

3-methoxymethyl-7[2-(2-amino-4-thiazolyl)-2-hydroxyiminoacetamido]-ceph-3-eme-4-carboxylic acid STEP A: Mixed anhydride of p-toluene sulfonic acid and the syn isomer of 2-(2-tritylamino-4-thiazolyl)-2-(1-methyl-1-methoxy)-ethoxyimino-acetic acid 1.05 g of tosyl chloride was added to a suspension or 3.01 g of the triethylamine salt of the syn isomer of 2-(2-tritylamino-4-thiazolyl)-2-(1-methyl-1-methoxy)-ethoxyiminoacetic acid in 15 ml of acetone and the mixture was stirred for 90 minutes. 20 ml of ether were added to the mixture which was cooled to −10° C. and vacuum filtered. The product was washed with ether to obtain 2.90 g of mixed anhydride of p-toluene sulfonic acid and the syn isomer of 2-(2-tritylamino -4-thiazolyl)-2-(1-methyl-1-methoxy)-ethoxyimino-acetic acid and triethylamine hydrochloride.

STEP B: Syn isomer of 3-methoxymethyl-7-[2-(2-tritylamino-4-thiazolyl)-2-{(1-methyl-1-methoxy)-ethoxyimino}-acetamido]-ceph-3-eme-4-carboxylic acid 2.4 g of the mixture of Step A were added to a solution of 0.732 g of 3-methoxymethyl-7-amino-ceph-3-eme-4-carboxylic acid, 0.84 g of triethylamine and 10 ml of methylene chloride cooled to −20° C. and the temperature was allowed to rise to room temperature. 0.5 ml of acetic acid was added to the mixture which was then washed with water, dried and evaporated to dryness. The residue was triturated with ether and was vacuum filtered to obtain 3.07 g of product which was crystallized from methanol to obtain 1.21 g of syn isomer of 3-methoxymethyl-7-[2-(2-tritylamino-4-thiazolyl)2-{(1-methyl -1-methoxy)-ethoxyimino}-acetamido]-ceph-3-eme-4-carboxylic acid.

NMR Spectrum (deuterochloroform):

Peaks at 1.52 ppm (hydrogens of geminal methyls); at 3.22–3.25 ppm (hydrogens of methoxy); at 3.45 pp.

(hydrogens of methylthio); at 4.25 ppm (hydrogens of $CH_2$—$OCH_3$) at 4.99 ppm (d; J=5) (6-hydrogen); at 5.73 ppm (dd; J=5 J=8) (7-hydrogen); at 6.70 ppm (5-hydrogen of syn thiazole); at 7.28 ppm (trityl)

STEP C: Syn isomer of 3-methoxymethyl-7-[2(2-amino-4-thiazolyl)-2-hydroximino-acetamido]-ceph-3-eme-4-carboxylic acid A mixture of 1.1 g of the product of Step B and 5 ml of aqueous formic acid was stirred at 45°-50° C. for 10 minutes and 2 ml of water were added thereto. The mixture was vacuum filtered and the filtrate was evaporated to dryness under reduced pressure at 30° C. while entraining the water with ethanol. The residue was crystallized from water and was vacuum filtered to obtain 0.54 g of raw product. The latter was dissolved in 5 ml of 50% aqueous ethanol containing trietylamie and the mixture was adjusted to a pH of 2 to 3 with formic acid. The mixture was vacuum filtered and the product was washed with ethanol and then with ether to obtain 0.44 g of solvated syn isomer of 3-methoxymethyl-7-[2(2-amino-4-thiazolyl)-2-hydroxyimino-acetamido]-ceph-3-eme-4-carboxylic acid.

Analysis: $C_{14}H_{15}O_6N_5S_2$. $0.5H_2O$; molecular weight=422.43;
Calculated: % C 39.9; % H 3.82; % N 16.58; % S 15.18;
Found: % C 40.0; % H 4.0; % N 16.1; % S 14.8.

IR Spectrum (Nujol):
Absorption at 1757 $cm^{-1}$ (carbonyl of β-lactam); at 1637-1638 $cm^{-1}$ (C=C, C=N); at 1605-1572-1488 $cm^{-1}$ (aromatic).

UV Spectrum (ethanol-0.1N HCl): inflex. towards 220 nm $E_{1cm}^{1\%}=288$. Max. at 262 nm $E_{1cm}^{1\%}=421$; $\epsilon=17,400$.

NMR Spectrum (DMSO):
Peaks at 3.20 ppm (hydrogens of methoxy); at 3.50 ppm (hydrogens of $SCH_2$—); at 4.17 ppm (hydrogens of —$CH_2O$—); at 5.14 ppm (d; J=5 6-hydrogen); at 5.77 ppm (dd; J=5; J=8 7-hydrogen); at 6.65 ppm (5-hydrogen of thiazole); at 7.1 ppm ($NH_2$); at 9.43 ppm (d; J=8 hydrogen of —NHCO).

EXAMPLE 2

Syn isomer of 1-oxo-propoxymethyl 3-methoxymethyl-7-[2-(2-amino-4-thiazolyl)-2-hydroxyimino-acetamido]-ceph-3-eme-4-carboxylate STEP A: Syn isomer of 1-oxo-propoxymethyl 3-methoxymethyl-7-[2-(2-tritylamino-4-thiazolyl)-2-{(1-methyl-1-methoxy)-ethoxyimino}-acetamido]-ceph-3-eme-4-carboxylate A mixture of 1.71 g of sodium iodide and 23 ml of anhydrous acetone was refluxed for 10 minutes to obtain a suspension of iodomethyl propionate which was immediately added at 0° C. over 10 minutes to a solution of 4.15 g of the syn isomer of 3-methoxymethyl-7-[2(2-tritylamino-4-thiazolyl)-2-{(1-methoxy-1-methyl)-ethoxyimino}-acetamido]-ceph-3-4-carboxylic acid, 0.456 g of dry potassium carbonate and 14 ml of anhydrous dimethylformamide and the suspension was stirred at 0° C. for 30 minutes, at 20° C. for 30 minutes and was then poured into a mixture of 340 ml of water, 17 ml of aqueous sodium bicarbonate solution and 50 ml of ethyl acetate. The mixture was stirred and extracted with ethyl acetate. The organic phase was washed with water, dried and evaporated to dryness under reduced pressure at less than 35° C. The residue was taken up in 25 ml of isopropyl ether and the mixture was vacuum filtered to obtain 4.42 g of syn isomer of 1-oxo-propoxymethyl 3-methoxymethyl-7-[2-(2-tritylamino-4-thiazolyl)-2-{(1-methyl-1-methoxy)-ethoxyimino}-acetamido]-ceph-3-eme-4-carboxylate.

NMR Spectrum (deuterochloroform):
Peaks at 1.15 ppm (t, J=7) and at 2.40 ppm (q, J=7) (ethyl); at 3.34 ppm (hydrogens of methoxy); at 3.55 ppm (hydrogens of —$SCH_2$—); at 4.33 ppm (hydrogens of —$CH_2$—$OCH_3$); at 5.05 ppm (d J=5 6-hydrogen); at 6.71 ppm (5-hydrogen of syn thiazole); at 7.33 ppm (trityl).

STEP B: Syn isomer of 1-oxopropoxymethyl 3-methoxymethyl-7-[2-(2-amino-4-thiazolyl)-2-hydroxyimino-acetamido]-ceph-3-eme-4-carboxylate A mixture of 4.37 g of the product of Step A in 22 ml of 65% aqueous formic acid was stirred at 45° to 50° C. for 15 minutes and was diluted with 90 ml of hot water. The mixture was vacuum filtered and the filtrate was evaporated to dryness under reduced pressure at less than 30° C. The residue was taken up in 100 ml of methylene chloride and the organic solution was washed with a saturated aqueous sodium chloride solution diluted to 0.1 and 7 ml of N sodium bicarbonate solution, was dried and evaporated to dryness under reduced pressure. The residue was taken up in 100 ml of ether and the mixture was vacuum filtered. The 2.10 g of raw product were taken up in 15 ml of ethyl acetate and the mixture was stirred for 30 minutes and was vaccum filtered. The recovered product was rinsed with ethyl acetate and then with ether to obtain 1.69 g of product. 1.57 g of the said product were dissolved in 15 ml of methylene chloride and the solution was filtered. The filtrate was evaporated to dryness under reduced pressure and the residue was taken up in 10 ml of ethyl acetate. The mixture was stirred for 30 minutes and was vacuum filtered. The recovered product was rinsed with ethyl acetate and with ether to obtain 1.29 g of syn isomer of 1-oxopropoxymethyl 3-methoxymethyl-7-[2-(2-amino-4-thiazolyl)-2-hydroxyimino-acetamido]-ceph-3-eme-4-carboxylate with a specific rotation of $[\alpha]_D^{20}=+52°\pm1°$ (c=1.5% in DMSO).

NMR Spectrum (deuterochloroform):
Peaks at 1.13 ppm (t: J=7) and at 2.41 ppm (q: J=7) (ethyl); at 3.30 ppm (hydrogens of methoxy); at 3.53 ppm (hydrogens of —$SCH_2$—); at 4.3 ppm (hydrogens of —$CH_2$—$OCH_3$); at 5.02 ppm (d: J=5 6-hydrogen); at 6.92 ppm (5-hydrogen of syn thiazole).

EXAMPLE 3

Syn isomer of 3-methoxymethyl-7-[2-(2-amino-4-thiazolyl)-2-methoxyimino-acetamideo]-ceph-3-eme-4-carboxylic acid STEP A: Mixed anhydride of p-toluene sulfonic acid and syn isomer of 2-(2-tritylamino-4-thiazolyl)-2-methoxyimino-acetic acid A mixture of 1.80 g of the triethylamine salt of the syn isomer of 2-(2-tritylamino-4-thiazolyl)-2-methoxyiminoacetic acid, 0.63 g of tosyl chloride and 20 ml of anhydrous acetone was stirred at 20° C. for one hour to obtain a suspension containing mixed anhydride of p-toluene sulfonic acid and syn isomer of 2-(2-tritylamino-4-thiazolyl)-2-methoxyimino-acetic acid what was used as is for the next step.

STEP B: Syn isomer of 3-methoxymethyl-7-[2-(2-tritylamino-4-thiazolyl)-2-methoxyimino-acetamido]-ceph-3-eme-4-carboxylic acid A solution of 0.732 g of 3-methoxymethyl-7-aminoceph-3-eme-4-carboxylic acid, 6.6 ml of 1N sodium bicarbonate solution and 3.4 ml of water was formed at 20° C. under an inert atmosphere and the suspension of Step A was added thereto at 5° C. over 5 minutes. The mixture was stirred at 0° to 5° C. for one hour and at 20° C. for one hour and was then filtered. The acetone was distilled under reduced pressure at not more than 30° C. and the mixture was acidified by addition of 0.7 ml of formic acid. The mixture was extracted with methylene chloride and the organic phase was washed with water, dried and evaporated to dryness under reduced pressure. The residue was taken up in 10 ml of ether and the mixture was vacuum filtered to obtain 1.75 g of syn isomer of 3-methoxymethyl-7-[2-(2-tritylamino-4-thiazolyl)-2-methoxyimino-acetamido]-ceph-3-eme-4-carboxylic acid which was used as is for the next step.

STEP C: Syn isomer of 3-methoxymethyl-7-[2-(2-amino-4-thiazolyl)-2-methoxyimino-acetamido]-ceph-3-eme-4-carboxlic acid A mixture of 1.07 g of the product of Step B and 8.4 ml of 66% aqueous formic acid was stirred at 45° to 50° C. under an inert atmosphere for 12 minutes and then b 3.4 ml of water were added at 45° to 50° C. and the mixture was vacuum filtered. The filtrate was evaporated to dryness under reduced pressure while entraining the water with ethanol and the residue was triturated with 10 ml of water. The mixture was vacuum filtered and the recovered product was rinsed with water, then with ether to obtain 0.436 g of product. Another 0.111 g of product was obtained from the mother liquors after purification for a total yield of 0.547 g. 0.542 g of the said product were taken up in 5.5 ml of water over one hour and the mixture was vacuum filtered. The product was rinsed with water and then with ether to obtain 0.453 g of product which was empasted with acetone. The mixture was vacuum filtered and the product was dried to obtain 0.379 g which was taken up in 10 ml of water, 0.83 ml of a 1 M sodium bicarbonate solution were slowly added to the mixture which was then diluted with 1 ml of 2M sodium chloride solution. The mixture was vacuum filtered and the filter was rinsed with water. The filtrate was acidified to a pH $\approx$3 by addition of 0.5 ml of 2 N hydrochloric acid and was vacuum filtered. The recovered product was rinsed with water, with ether and was empasted with acetone to obtain 0.227 g of syn isomer of 3-methoxymethyl-7-[2(2-amino-4-thiazolyl)-2-methoxyimino-acetamido]-ceph-3-eme-4-carboxylic acid.

Analysis: $C_{15}H_{17}O_4N_5S_2$: molecular weight = 427.459:

Calculated: % C 42.15; % H 4.01; % N 16.38; % S 15.00;

Found: % C 42; % H 3.9; % N 15.8; % S 15.2.

IR Spectrum (Nujol):

Absorption at 1756 cm$^{-1}$ ($\beta$-lactam carbonyl); at 1660 cm$^{-1}$ (amide); at 1637, 1623 and 1562 cm$^{-1}$ (C=C, C=N conjugated + amide II COO−); at 1031 cm$^{-1}$ (C=NOR).

UV Spectrum (0.1N HCl in ethanol): Inflex. towards 244 nm $E_1^1$ = 355; Max. at 262 nm $E_1^1$ = 437; $\epsilon$ = 18.700

NMR Spectrum (DMSO):

Peaks at 3.22 ppm (hydrogens of methoxy); at 3.85 ppm (N—O—CH$_3$); at 3.53 ppm (hydrogens of —CH$_2$S); at 4.18 ppm (hydrogens of —CH$_2$—OCH$_3$); at 5.14 ppm (d; J=5 6-hydrogen); at 5.76 ppm (d,d; J=5, J=8 7-hydrogen); at 6.76 ppm (5-hydrogen of syn thiazole); at 9.60 ppm (d; J=8 NHCO).

EXAMPLE 4

Syn isomer of 3-methylthiomethyl-7-[2-(2-amino-4-thiazolyl)-2-hydroxyimino-acetamido]-ceph-3-eme-4-carboxylic acid

STEP A: Syn isomer of 3-methylthiomethyl-7-[2-(2-tritylamino-4-thiazolyl)-2-{(1-methyl-1-methoxy-ethoxyimino}-acetamido]-ceph-3-eme-4-carboxylic acid 9.5 g of the mixed anhydride of p-toluene sulfonic acid and the syn isomer of 2-(2-tritylamino-4-thiazolyl)-2-[(1-methyl-1-methoxy)-ethoxyimino]-acetic acid were added at −20° C. to a mixture of 2.60 g of 3-methylthiomethyl-7-amino-ceph-3-eme-4 -carboxylic acid, 37.5 ml of methylene chloride and 2.8 ml of triethylamine and the mixture was stirred at 0° C. for 2 hours. The mixture was acidified with 1.75 ml of acetic acid and the organic phase was washed with water, dried and evaporated to dryness under reduced pressure. The residue was taken up in 50 ml of ether and the mixture was vacuum filtered. The product was rinsed with ether to obtain 8.45 g of raw product which was taken up in 45 ml of methanol. The mixture was stirred for 30 minutes and crystallization was induced. The mixture was vacuum filtered and the recovered product was rinsed with methanol and then with ether to obtain 5.2 g of syn isomer of 3-methylthiomethyl-7-[2-(2-tritylamino-4-thiazolyl) -2-{(1-methyl-1-methoxy-ethoxyimino)-acetamido]-ceph-3-eme-4-carboxylic acid.

NMR Spectrum (deuterochloroform):

Peaks at 1.85 ppm (hydrogens of methylthio); at 5.05 ppm (d; J=5 6-hydrogen); at 5.70 ppm (d,d; J=5, J=8 7-hydrogen); at 6.71 ppm (5-hydrogen of syn thiazole); at 7.28 ppm (trityl).

STEP B: Syn isomer of 3-methylthiomethyl-7-[2-(2-amino-4-thiazolyl)-2-hydroxyimino-acetamido]-ceph-3-eme-4-carboxylic acid A mixture of 3.72 g of the product of Step A, and 18.6 and of 66% aqueous formic acid was stirred at 50° C. for 10 minutes and then 7.4 ml of water were added thereto. The mixture was vacuum filtered and the filtrate was distilled to dryness under reduced pressure at not more than 30° C. while effecting 2 entrainments with a 2–1 ethanol-water mixture. The residue was taken up in 10 ml of water and the mixture was vacuum filtered. The product was rinsed with water and then ether to obtain 1.945 g of raw product which was taken up in 136 ml of 50% aqueous ethanol. 0.63 ml of triethylamine were slowly added thereto and the mixture was vacuum filtered. The filtrate was acidified at a pH of $\approx$3–4 by addition of 0.45 ml of 50% aqueous formic acid and was vacuum filtered. The product was rinsed with 50% aqueous ethanol, anhydrous ethanol and finally ether to obtain 1.392 g of syn isomer of 3-methylthiomethyl-7-

[2-(2-amino-4-thiazolyl)-2-hydroxyiminoacetamido]-ceph-3-eme-4-carboxylic acid.

IR Spectrum (Nujol):

Absorption at 1772 cm$^{-1}$ ($\beta$-lactam carbonyl); at 1693 cm$^{-1}$ (amide); at 1619 cm$^{-1}$ (NH$_2$ formation); at 1595 and 1535 cm$^{-1}$ (aromatic).

UV Spectrum (0.1N HCl in ethanol): Inflex. towards 220 nm $E_1^1 = 320$; Max. at 262 nm $E_1^1 = 444$; $\epsilon = 19.100$.

NMR Spectrum (deuterochloroform):

Peaks at 1.98 ppm (hydrogens of CH$_3$S—); at 3.58 ppm (hydrogens of —CH$_2$S—); at 5.17 ppm (d; J=5 6-hydrogen); at 5.72 ppm (d,d; J=5, J=8 7-hydrogen); at 6.66 ppm (5-hydrogen of syn thiazole); at 9.43 ppm (d; J=8 NHCO).

EXAMPLE 5

Syn isomer of 1-oxopropoxymethyl 3-methylthiomethyl-7-[2-(2-amino-4-thiazolyl)-2-hydroxyimino-acetamido]-ceph-3-eme-4-carboxylate STEP A: Syn isomer of 1-oxopropoxymethyl 3-methylthiomethyl -7-[2-(2-tritylamino-4-thiazolyl)-2-{(1-methyl-1-methoxy)-ethoxyimino) -acetamido]-ceph-3-eme-4-carboxylate A mixture of 5.2 g of the syn isomer of Step A of Example 4, 0.56 g of potassium carbonate and 20 ml of anhydrous dimethylformamide was stirred at 20° C. and after cooling to 5° C., 28 ml of a suspension of iodomethyl propionate in acetone prepared from 1.715 g of chloromethyl propionate were added thereto at 5° to 10° C. The mixture was stirred for 30 minutes at 5° and at 20° C. for 30 minutes and was then poured with stirring into a solution of 260 ml of water, 50 ml of ethyl acetate and 20 ml of aqueous N sodium bicarbonate solution at 10° to 15° C. The aqueous phase was extracted with ethyl acetate and the organic extract phase was washed with water, dried and evaporated to dryness under reduced pressure. The residue was taken up in 50 ml of isopropyl ether and the mixture was vacuum filtered to obtain 5.53 g of syn isomer of 1-oxopropoxymethyl 3-methylthiomethyl-7-[2-(2-tritylamino-4-thiazolyl)-2-{(1-methyl-1-methoxy)-ethoxyimino}-acetamido]-ceph-3-eme-4-carboxylate.

STEP B: Syn isomer of 1-oxopropoxymethyl 3-methylthiomethyl-7-[2-(2-amino-4-thiazolyl)-2-hydroxyimino-acetamido]-ceph-3-eme-4-carboxylate A mixture of 3.75 g of the product of Step A and 18.7 ml of 66% aqueous formic acid was stirred at 50° C. for 10 minutes and then 7.5 ml of water were added thereto. The mixture was vacuum filtered and the filtrate was evaporated to dryness under reduced pressure at not more than 30° C. while entraining twice with a 2-1 methanol-water mixture. The residue was taken up in 10 ml of water and the mixture was vacuum filtered. The product was rinsed with water then with ether to obtain 2.17 g of raw product. The latter was chromatographed over silica gel and was eluted with a 3-1 ethyl acetate-acetone mixture. The product was taken up in 10 ml of isopropyl ether and the mixture was vacuum filtered to obtain 1.55 of product. The latter was taken up in 4.5 ml of ethyl acetate and the mixture was added to 7.5 ml of ethyl acetate and the mixture was vacuum filtered. The product was rinsed with ethyl acetate and then isopropyl ether to obtain 0.536 g of syn isomer of 1-oxopropoxymethyl 3-methylthiomethyl-7-[2-(2-amino-4-thiazolyl)-2-hydroxyimino-acetamido]-ceph-3-eme-4-carboxylate.

UV Spectrum (ethanol): Max. at 222 nm $E_1^1 = 384$; $\epsilon = 19,800$; Max. at 262 nm $E_1^1 = 271$; $\epsilon = 14,8000$.

UV Spectrum (0.1N HCl in ethanol): Inflex. towards 218 nm $E_1^1 = 293$; Max. at 263 nm $E_1^1 = 382$; $\epsilon = 19,700$.

IR Spectrum (Nujol): Absorption at 1779 cm$^{-1}$ ($\beta$-lactam carbonyl); at 1738 and 1759 cm$^{-1}$ (ester+propionate); at 1664 cm$^{-1}$ (amide); at 1613 cm$^{-1}$ (NH$_2$ formation); at 1528 cm$^{-1}$ (thiazole+amide).

NMR Spectrum (deuterochloroform): Peaks at 1.17 ppm and 2.42 ppm (t; J=7 q; J=7 ethyl); at 2.1 ppm (CH$_3$S—); at 5.11 ppm (d; J=5 6-hydrogen); at 5.9 ppm (hydrogens of —COOCH$_2$O—); at 7.1 ppm (5-hydrogen of thiazole).

EXAMPLE 6

Syn isomer of 3-methylthiomethyl-7-[2-(2-amino-thiazolyl)-2-methoxyimino-acetamido]-ceph-3-eme-4-carboxylic acid STEP A: Syn isomer of 3-methylthiomethyl-7-[2-(2-tritylamino-4-thiazolyl)-2-methoxyimino-acetamido]-ceph-3-eme-4-carboxylic acid A mixture of 2.6 g of 3-methylthiomethyl-7-amino-ceph -3-eme-4-carboxylic acid, 26 ml of methylene chloride and 3 ml of triethylamine was stirred at 20° C. under an inert atmosphere and after cooling the mixture to $-20°$ C., an acetone suspension of the mixed anhydride of Example 3 prepared from 6 g of the triethylamine salt of the syn isomer of 2-(2-tritylamino-4-thiazolyl)-2-methoxyimino-acetic acid was added thereto. The mixture was stirred for 2 hours at 0° C. and was then acidified with 1 ml of acetic acid. The mixture was evaporated to dryness under reduced pressure and the residue was taken up in 50 ml of methylene chloride. The organic solution was washed with water, dried and evaporated to dryness under reduced pressure. The residue was taken up in 50 ml of ether and the mixture was vacuum filtered to obtain 8.06 g of syn isomer of 3-methylthiomethyl-7-[2-(2-tritylamino-4-thiazolyl)-2-methoxyimino-acetamido]-ceph-3-eme-4-carboxylic acid.

STEP B: Syn isomer of 3-methylthiomethyl-7-[2-(2-amino-4-thiazolyl)-2-methoxyimino-acetamido]-ceph-3-eme-4-carboxylic acid A mixture of 6.15 g of the product of Step A and 61 ml of trifluoroacetic acid was stirred at 20° C. for 20 minutes and the mixture was evaporated under reduced pressure at 30° C. to a volume of 15 ml. 150 ml of ispropyl ether were added at 10° C. to the mixture which was then stirred at 20° C. for 15 minutes and was vacuum filtered. The 3.2 g of raw product were chromatographed over silica gel and were eluted with aqueous 2M sodium chloride solution containing 4% of 1M sodium bicarbonate solution. The raw product was dissolved in a mixture of 10 ml of eluant, 1.4 ml of aqueous 1M sodium bicarbonate solution, 1 ml of triethylamine and 1 ml of aqueous saturated sodium chloride solution and the solution was acidified to a pH of 3 by addition of 50% aqueous formic acid. The mixture was vacuum filtered and the product was washed with water and then with ether to obtain 0.99 g of syn isomer of 3-methylthiomethyl-7-[2-(2-amino-4-thiazolyl)-2- methoxyimino-acetamido]-ceph-3-eme-4-carboxylic acid.

Analysis: $C_{15}H_{17}O_5N_5S_3$; molecular weight=443.524; Calculated: %C 40.62; %H 3.86; %N 15.79; %S 21.69; Found: %C 40.1; %H 3.8; %N 15.5; %S 20.8.

IR Spectrum (Nujol): Absorption at 1770 cm$^{-1}$ shoulder and 1760 cm$^{-1}$ max ($\beta$-lactam carbonyl); at 1660 cm$^{-1}$ (amide); at 1628 cm$^{-1}$ (COO+NH$_2$ formation); at 1545 and 1529 cm$^{-1}$ (amide II+thiazole).

UV Spectrum (ethanol): Max. at 235 nm $E_1^1=389$; $\epsilon=17,300$; Inflex. towards 255 nm $E_1^1=343$; $\epsilon=15,200$; Inflex. towards 280 nm $E_1^1=236$.

UV Spectrum (0.1N HCl in ethanol): Max. at 266 nm $E_1^1=427$; $\epsilon=18,900$; Inflex. towards 280 nm $E_1^1=364$.

RNM Spectrum (DMSO): Peaks at 1.98 ppm (CH$_3$S); at 3.62 ppm (CH$_2$S); at 3.85 (OCH$_3$); at 5.02 ppm (6-hydrogen); at 5.74 (d,d; J=5, J=8 7-hydrogen); at 6.78 ppm (5-hydrogen of thiazole); at 9.62 ppm (d; J=8 NHCO).

EXAMPLE 7

Syn isomer of 3-ethylthiomethyl-7-[2-(2-amino-4-thiazolyl)-2-hydroxyimino-acetamido]-ceph-3-eme-4-carboxylic acid

STEP A:
3-ethylthiomethyl-7-amino-ceph-3-eme-4-carboxylic acid 170 ml of the etherate of boron trifluoride and then 45 ml of ethanediol were added to a mixture of 54.4 g of 7-amino-cephalosporanic acid and 544 ml of acetic acid and the mixture was stirred at 45°–50° C. for 2 hours and was then cooled to 20° to 30° C. 170 ml of triethylamine were added to the mixture which was then vacuum filtered. The product was rinsed with acetic acid, with acetone and then with ether to obtain 32.45 g of 3-ethylthiomethyl-7-amino-ceph-3-eme-4-carboxylic acid.

UV Spectrum (0.1N HCl-ethanol): Max. at 262 nm $E_1^1=217$; $\epsilon=5,950$.

NMR Spectrum (DMSO): Peaks at 1.13 ppm (t; J=7) and 2.46 ppm (q; J=7)(—S—CH$_2$—CH$_3$); at 3.6 ppm (—CH$_2$—S—); at 4.72–4.79 ppm and 4.98–5.05 ppm (hydrogen of $\beta$-lactam).

STEP B: Syn isomer of 3-ethylthiomethyl-7-[2-(2-trityl-amino-4-thiazolyl)-2-hydroxyimino-acetamido]-ceph-3-eme-4-carboxylic acid A solution of 1.37 g of the product of Step A, 1.75 ml of triethylamine and 15 ml of methylene chloride at room temperature under an inert atmosphere was cooled to −30° C. and 3.97 g of the mixed anhydride of tosyl and the syn isomer of 2-(2-tritylamino-4-thiazolyl)-2-{(1-methyl-1-methoxy)-ethoxyimino}-acetic acid were added thereto all at once. The temperature was allowed to rise to 0° C. and was stirred for 2 hours at 0° C. The mixture was neutralized by the addition of 0.75 ml of acetic acid and was extracted with methylene chloride. The organic phase was washed with water, dried and evaporated to dryness under reduced pressure at less than 30° C. The residue was triturated with 20 ml of ether and was vacuum filtered to obtain 3.55 g of product which was crystallized from methanol to obtain 2.17 g of syn isomer of 3-ethylthiomethyl-7-[2-(2-trityl-amino-4-thiazolyl)-2-hydroxyimino-acetamido]-ceph-3-eme-4-carboxylic acid.

STEP C: Syn isomer of 3-ethylthiomethyl-7-[2-(2-amino-4-thiazolyl)-2-hydroxyimino-acetamino]-ceph-3-eme-4-carboxylic acid A solution of 2.16 g of the product of Step B and 10.8 ml of 66% aqueous formic acid was stirred at 50° C. for 10 minutes and 4.3 ml of water were added thereto. The mixture was vacuum filtered and the filtrate was evaporated to dryness under reduced pressure at less than 35° C. The residue was taken up in 6 ml of water and was then vacuum filtered. The product was dried to obtain 1.168 g of product which was dissolved in 6 ml of water and 0.4 ml of triethylamine. The crystallized triethylamine salt was added to 10 ml of water and the mixture was filtered. The filter was rinsed with 5 ml of methanol and the filtrate was added to 11 ml of ethanol. The mixture was acidified to a pH of 3–4 by addition of 1 ml of 50% aqueous formic acid and stood for 30 minutes at 20° C. and was then vacuum filtered. The product was rinsed with anhydrous ethanol and then with ether to obtain 0.885 g of syn isomer of 3-ethylthiomethyl-7-[2(2-amino-4-thiazolyl)-2-hydroxyimino-acetamido]-ceph-3-eme-4-carboxylic acid.

UV Spectrum (0.1N HCl-ethanol): Inflex. towards 218 nm $E_1^1=320$; Max. at 263 nm $E_1^1=448$; $\epsilon=19,900$.

NMR Spectrum (DMSO): Peaks at 1.15 ppm (t; J=7) and 2.62 ppm (q; J=7)(—S—CH$_2$—CH$_3$); at 3.61 ppm (—CH$_3$—CH$_2$—S—CH$_2$—); at 11.4 ppm (N—OH); at 6.75 ppm (5-hydrogen of thiazole); at 5.12–5.2 ppm (6-hydrogen); at 5.61–5.7 ppm and 5.75–5.83 ppm (7-hydrogen); at 9.62–9.48 ppm (NH—C═O).

EXAMPLE 8

Syn isomer of 3-ethoxymethyl-7-[2-(2-amino-4-thiazolyl)-2-hydroxyimino-acetamido]-ceph-3-eme-4-carboxylic acid

STEP A:
3-ethoxymethyl-7-amino-ceph-3-eme-4-carboxylic acid 128 ml of the etherate of boron trifluoride and then 71 ml of ethanol were added with stirring to a mixture of 27.2 g of 7-amino-cephalosporanic acid and 272 ml of anhydrous acetonitrile and the mixture was heated at 45°–50° C. under an inert atmosphere. The mixture was cooled to 15°–20° C. and 98 ml of triethylamine were added thereto over 15 minutes. The mixture was vacuum filtered and the product was rinsed with acetonitrile, acetone and then ether to obtain 19.25 g of raw product 18 g of which was dissolved in 54 ml of 2N hydrochloric acid. The solution was heated to 45° C., treated with activated carbon and filtered. The filtrate was neutralized hot by addition of 11 ml of ammonium hydroxide solution and was vacuum filtered at 20° C. The product was rinsed with water, acetone and then ether to obtain 8.6 g of product, 5.86 g of the said product were taken up in 24 ml of 2N hydrochloric acid and the mixture was stirred at 45° C. for one hour. 4 ml of hot ammonium hydroxide were added thereto and the mixture was vacuum filtered at 20° C. The product was rinsed with water, acetone and then ether to obtain 4.75 g of 3-ethoxymethyl-7-amino-ceph-3-eme-4-carboxylic acid.

UV Spectrum (0.1N HCl-ethanol): Max. at 259 nm $E_1^1=239$; $\epsilon=6,200$.

NMR Spectrum (DMSO): Peaks at 1.08 ppm (t: J=7) and at 3.39 ppm (q: J=7) (—OCH$_2$—CH$_3$); at 4.18 ppm (O—CH$_2$—); at 4.72–4.8 ppm and 4.93–5.03 ppm (6- and 7-hydrogens).

STEP B: Syn isomer of 3-ethoxymethyl-7-[2-(2-tritylamino-4-thiazolyl)-2-1-methoxy 1-methyl ethoxyimino-acetamido]ceph-3-eme-4-carboxylic acid.

Using the procedure of Step B of Example 7, 1.29 g of the product of Step A was reacted to obtain 3.74 g of raw product which was crystallized from ethyl acetate to obtain 1.791 g of syn isomer of 3-ethoxymethyl-7-[2-(2-tritylamino-4-thiazolyl)-2-]1-methoxy 1-methyl ethoxyimino acetamdio/-ceph 3-eme-4-carboxylic acid.

UV Spectrum (ethanol): Inflex. towards 230 nm $E_1^1=370$; Inflex. towards 260 nm $E_1^1=233$; $\epsilon=17,300$; Inflex. towards 300 nm $E_1^1=80$; $\epsilon=5,900$.

UV Spectrum (0.1N HCl-ethanol): Max. at 271 nm $E_1^1=256$; $\epsilon=19,000$.

NMR Spectrum (deuterochloroform): Peaks at 1.05–1.13–1.21 ppm and 3.23–3.31–3.38–3.47 ppm (—OCH$_2$—CH$_3$); at 1.54 ppm (geminal methyls); at 3.24 ppm (methoxy); at 3.51 ppm (—S—CH$_2$—); at 4.15 ppm (—CH$_2$—O); at 4.98–5.05 ppm (6-hydrogen); at 5.68 to 5.87 ppm (7-hydrogen); at 6.75 ppm (5-hydrogen of thiazole).

STEP C: Syn isomer of 3-ethoxymethyl-7-[2-(2-amino-4-thiazolyl)-2-hydroxyimino-acetamido]-ceph-3-eme-4-carboxylic acid A solution of 1.735 g of the product of Step B and 8.6 ml of 66% aqueous formic acid was heated at 50° C. for 10 minutes and 3.5 ml of hot water were added thereto. The mixture was vacuum filtered and the filtrate was evaporated to dryness under reduced pressure. The residue was taken up in 5 ml of 50% aqueous ethanol and the solution was evaporated to dryness at less than 35° C. The residue was taken up in 6 ml of water and was triturated and vacuum filtered. The product was rinsed with water and then with ether to obtain 0.915 g of raw product 0.813 g of which was dissolved in 10 ml of 50% aqueous ethanol and 0.45 ml of triethylamine. The mixture was filtered and the filter was rinsed with 6 ml of aqueous ethanol. The filtrate was acidified to a pH of 3.4 by addition of 0.7 ml of 50% aqueous formic acid and crystallization was induced. The mixture was vacuum filtered and the product was rinsed with aqueous ethanol and then with ether to obtain 0.688 g of syn isomer of 3-ethoxymethyl-7-[2-(2-amino-4-thiazolyl)-2-hydroxyimino-acetamido]-ceph-3-eme-4-carboxylic acid.

UV Spectrum (0.1N HCl-ethanol): Inflex. towards 219 nm $E_1^1=288$; $\epsilon=12,300$; Max. at 261 nm $E_1^1=409$; $\epsilon=17,500$.

NMR Spectrum (DMSO): Peaks at 1.11 ppm (t: J=7) and at 3.40 ppm (q: J=7)(—OCH$_2$—CH$_3$); at 4.22 ppm (—CH$_2$O—); at 5.11–5.19 ppm (6-hydrogen); at 5.67–5.75–5.8–5.87 ppm (7-hydrogen); at 6.75 ppm (5-hydrogen of thiazole); at 7.17 ppm (—NH$_2$—); at 9.47–9.6 ppm (NHCO).

EXAMPLE 9

Syn isomer of 3-(2-propenyloxymethyl)-7-[2-(2-amino-4-thiazolyl)-2-methoxyimino-acetamido]-ceph-3-eme-4-carboxylic acid

STEP A: 3-allyloxymethyl-7-amino-ceph-3-eme-4-carboxylic acid

Using the procedure of Step A of Example 8, 27.2 g of 7-amino-cephalosporanic acid, 170 ml of the etherate of boron trifluoride, 136 ml of allyl alcohol and 115 ml of triethylamine were reacted and the 9 g of raw product was purified successively twice with hot hydrochloric acid and ammonium hydroxide to obtain 4.72 g of 3-allyloxymethyl-7-amino-ceph-3-eme-4-carboxylic acid.

UV Spectrum (0.1N HCl-ethanol): Max. at 259–260 nm $E_1^1=244$; $\epsilon=6,600$.

NMR Spectrum (DMSO): Peaks at 4.23 ppm (—CH$_2$O); at 5.62 to 6.25 ppm (hydrogen of —O—CH=CH$_2$); at 4.72–4.8 ppm and 4.95–5.03 ppm (hydrogen of β-lactam). STEP B: Syn isomer of 3-(2-propenyloxymethyl)-7-[2-(2-amino-4-thiazolyl)-2-methoxyimino-acetamido]-ceph-3-eme-4-carboxylic acid 0.67 ml of triethylamine was added with stirring at −20° C. to a mixture of 0.96 g of the sym isomer of 2-(2-amino-4-thiazolyl)-2-methoxyimino-acetic acid, 0.912 g of tosyl chloride and 4 ml of anhydrous dimethylacetamide and the mixture was stirred at −20° C. for one hour. A solution cooled to −65° to −70° C. obtained by reacting 0.992 g of the product of Step A, 10 ml of methylene chloride and 1.5 ml of triethylamine at 15° to 20° C. were added over 5 minutes to the mixture cooled to −20° C. and the mixture was stirred at −65°±2° C. for 30 minutes 2 ml of a 1—1 acetic acid-methylene chloride were added thereto and the mixture was stirred for 15 minutes at −65° C. after which the temperature was allowed to rise to −50° C. 2 ml of water were added to the mixture and after the temperature rose to 0° C., 4 ml of 50% aqueous formic acid were added thereto. The methylene chloride was distilled under reduced pressure at less than 30° C. and 11 ml of water were added thereto followed by the addition of 50 ml of aqueous saturated sodium chloride solution. The aqueous phase was decanted and the gummy precipitatic was empasted with 5 ml of water. The mixture was vacuum filtered and the product was rinsed with water and with ether to obtain 0.728 g of raw product. The various aqueous phases were added to 20 ml of aqueous saturated sodium chloride solution and the mixture was extracted with methyl acetate. The organic phase was dried and evaporated to dryness and the residue was taken up in 20 ml of aqueous saturated sodium chloride solution. The precipitate was empasted with 5 ml of water to obtain 0.338 g of raw product which was chromatographed over silica gel. Elution with 2M sodium chloride solution containing 4°/$_{oo}$ of 1M sodium bicarbonate solution yielded 1.060 g of raw product. The aqueous fractions were acidified to a pH of 3 to 4 with 50% aqueous formic acid and was vacuum filtered to obtain 0.18 g of syn isomer of 3-(2-propenyloxymethyl)-7-[2-(2-amino-4-thiazolyl)-2-methoxyimino-acetamido]-ceph-3-eme-4-carboxylic acid. Another 0.368 g of the said product was obtained from the filtrate by extraction with methyl acetate as before.

UV Spectrum (0.1N HCl-ethanol): Max. at 265 nm $E_1^1=423$; $\epsilon=19,200$.

NMR Spectrum (DMSO): Peaks at 3.84 ppm (N—O—CH$_3$); at 3.86–3.93 ppm (hydrogens of O—CH$_2$—CH=); at 4.24 ppm (—CH$_2$O); at 5.13 to 5.33 ppm (=CH$_2$ and 6-hydrogen); at 5.7 to 6.1 ppm (7-hydrogen and hydrogen of —CH=CH$_2$); at 6.72 ppm (5-hydrogen of thiazole); at 9.5–9.6 ppm (—NHCO—).

EXAMPLE 10

Syn isomer of 3-propoxymethyl-7-[2-(2-amino-4-thiazolyl)-2-methoxyimino-acetamido]-ceph-3-eme-4-carboxylic acid

STEP A:
3-propoxymethyl-7-amino-ceph-3-eme-4-carboxylic acid

Using the procedure of Step A of Example 8, 27.2 g of 7-amino-cephalosporanic acid, 170 ml of the etherate of of boron trifluoride, 131 ml of propanol and 128 ml of triethylamine were reacted to obtain 17.4 g of raw product which was purified with hot hydrochloric acid and ammonium hydroxide to obtain 7.45 g of 3-propoxymethyl-7-amino-ceph-3-eme-4-carboxylic acid.

UV Spectrum (0.1N HCl- ethanol): Max. at 259 nm $E_1^1 = 238$; $\epsilon = 6,500$.

NMR Spectrum (DMSO): Peaks at 0.72–0.85–0.97 ppm ($CH_3$—); at 1.2 to 1.8 ppm (hydrogens of $CH_3$—$CH_2$—); at 3.2-3.3-3.4 ppm (hydrogens of —O—$CH_2$—$CH_2$—); at 4.2 ppm (hydrogens of —$CH_2$—O—$C_3H_7$); at 4.7–4.78 ppm and 4.95–5.03 ppm (6- and 7-hydrogens).

STEP B: Syn isomer of 2-propoxymethyl-7-[2-(2-amino-4-thiazolyl)-2-methoxyimino-acetamido]-ceph-3-eme-4-carboxylic acid A mixture of 1.440 g of the syn isomer of 2-(2-amino-4-thiazolyl)-2-methoxyimino-acetic acid, 1.368 g of tosyl chloride and 6 ml of anhydrous dimethyacetamide was cooled to $-15°$ to $-20°$ C. under an inert atmosphere and 1 ml of triethylamine was added over 2 minutes at $-15°$ to $-20°$ C. The mixture was stirred for one hour at $-15°$ to $-20°$ C. and a solution cooled to $-65°$ to $-70°$ C. and obtained by reacting 1.5 g of the product of Step A, 2.25 ml of triethylamine and 15 ml of methylene chloride at 15° to 20° C. was added over 5 minutes to the mixture at $-20°$ C. The mixture was stirred at $-65° \pm 2°$ C. for 30 minutes and then 3 ml of a 1—1 acetic acid-methylene mixture were added thereto. The mixture was stirred at $-65°$ C. for 15 minutes and after the temperature rose to $-50°$ C., 3 ml of water were added thereto. AT 0° to 5° C., 6 ml of a 50% aqueous formic acid were added thereto and the methylene chloride was distilled under reduced pressure at less than 30° C. while adding 165 ml of water. Then 25 ml of water and 25 ml of an aqueous saturated sodium chloride solution were added to the mixture which was then extracted with ethyl acetate. The organic phase was washed with an aqueous half saturated sodium chloride solution, was treated with activated carbon, dried and evaporated to dryness under reduced pressure. The residue was taken up in 100 ml of aqueous saturated sodium chloride solution and the aqueous phase was decanted. The gummy residue was empasted with 5 ml of water to solidify the product and the mixture was vacuum filtered. The product was rinsed with water and then with ether to obtain 1.682 g of raw product. The wash waters were extracted with methyl acetate and the organic phase was dried and evaporated to dryness. The residue was taken up in 50 ml of aqueous saturated sodium chloride solution and the mixture was vacuum filtered to obtain 0.538 g of raw product. The latter was taken up in 20 ml of water and the solution was extracted with methyl acetate. The organic phase was dried and evaporated to dryness under reduced pressure. The residue was triturated with 5 ml of ether and was vacuum filtered to obtain 0.450 g of syn isomer of 2-propoxymethyl-7-[2-(2-amino-4-thiazolyl)-2-methoxyimino-acetamido]-ceph-3-eme-4-carboxylic acid.

UV Spectrum (ethanol): Max. at 237 nm $E_1^1 = 359$; $\epsilon 16,400$; Inflex. towards 251 nm $E_1^1 = 322$; $\epsilon = 14,700$; Inflex. towards 290 nm $E_1^1 = 157$.

UV Spectrum (0.1N HCl-ethanol): Max. at 263 nm $E_1^1 = 388$; $\epsilon = 17,700$.

NMR Spectrum (DMSO): Peaks at 0.85 ppm (t: $J = 7$)($CH_3$— of propyl); at 3.32 ppm (t:$J = 7$)(hydrogens of —$OCH_2$—$CH_2$—); at 4.23 ppm (—$CH_2O$—); at 5.12–5.2 ppm (6-hydrogen); 5.65–5.73 ppm and 5.78–5.87 ppm (7-hydrogen); at 6.81 ppm (5-hydrogen of thiazole); at 3.9 ppm (—N—O—$CH_3$); at 3.55 ppm (—$CH_2$—S—); at 9.58-9.72 ppm (NHCO).

EXAMPLE 11

Syn isomer of 3-ethoxymethyl-7-[2-(2-amino-4-thiazolyl)-2-methoxyimino-acetamido]-ceph-3-eme-4-carboxylic acid Using the procedure of Example 9, 0.949 g of 3-ethoxymethyl-7-amino-ceph-3-eme-4-carboxylic acid were reacted up to the stage of removal of methylene chloride and addition of water. The mixture was added to 60 ml of aqueous saturated sodium chloride solution and was vacuum filtered. The product was rinsed with water and then with ether to obtain 0.250 g of raw product. The wash waters were extracted with methyl acetate and the organic phase was dried and evaporated to dryness. The residue was taken up in 50 ml of aqueous saturated sodium chloride solution and the mixture was filtered. The product was empasted with 5 ml of water and was vacuum filtered to obtain 0.361 g of raw product.

The first fraction was chromatographed over silica gel and was eluted with a 2M sodium chloride solution containing 4°/$_{oo}$ of 1M sodium bicarbonate solution. The desired fractions were acidified to a pH of 3 to 4 by addition of 50% aqueous formic acid and the organic phase was dried and evaporated to dryness. The residue was taken up in 5 ml of ether, triturated and vacuum filtered to obtain 0.122 g of product. The latter product and the second fraction were taken up in 5 ml of water and 1.4 ml of 1M sodium bicarbonate solution and the mixture was treated with activated carbon and acidified to a pH of 3 to 4 by addition of 0.3 ml of 50% aqueous formic acid. The mixture was extracted with methyl acetate and the organic extract was dried and evaporated to dryness. The residue was taken up in ether and filtered to obtain 0.366 g of syn isomer of 3-ethoxymethyl-7-[2-(2-amino-4-thiazolyl)-2-methoxyimino-acetamido]-ceph-3-eme-4-carboxylic acid.

UV Spectrum (ethanol): Max. at 235 nm $E_1^1 = 411$; $\epsilon = 18,100$; Inflex. towards 251 nm $E_1^1 = 361$; $\epsilon = 15,900$; Inflex. towards 290 nm $E_1^1 = 174$.

U.V. Spectrum (0.1N HCl in ethanol): Max. at 263-264 nm $E_1^1 = 429$; $\epsilon = 18,900$.

NMR Spectrum (DMSO): Peaks at 1.11 ppm (t: J=7) and at 3.28-3.35 ppm and 3.37-3.51 ppm (O—CH$_2$—CH$_3$); at 3.83 ppm (NOCH$_3$); at 3.80 ppm (—OCH$_2$—); at 5.11-5.17 ppm (6-hydrogen); at 5.68-5.73 ppm and 5.77-5.82 ppm (7-hydrogen); at 6.73 ppm (5-hydrogen of thiazole); at 9.51-9.6 ppm (NHCO).

EXAMPLE 12

Syn isomer of 3-isopropoxymethyl-7-[2-(2-amino-4-thiazolyl)-2-methoxyimino-acetamido]-ceph-3-eme-4-carboxylic acid

STEP A:
3-isopropoxymethyl-7-amino-ceph-3-eme-4-carboxylic acid

Using the procedure of Step A of Example 8, 27.2 g of 7-amino-cephalosporanic acid, 170 ml of the etherate of boron trifluoride, 134 ml of isopropanol and 125 ml of triethylamine were reacted to obtain 16.25 g of raw product which was purified by two successive treatments with hot hydrochloric acid and ammonium hydroxide to obtain 5.8 g of 3-isopropoxymethyl-7-amino-ceph-3-eme-4-carboxylic acid.

UV Spectrum (0.1N HCl-ethanol): Max. at 259 nm $E_1^1=233$; $\epsilon=6,300$.

NMR Spectrum (DMSO): Peaks at 1.02-1.12 ppm (hydrogens of

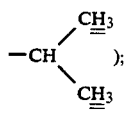

at 4.2 ppm (—CH$_2$O—); at 4.7-4.8 ppm and 4.95-5.03 ppm (6- and 7-hydrogens).

STEP B: Syn isomer of 3-(isopropoxymethyl-7-[2-(2-amino-4-thiazolyl)-2-methoxyimino-acetamido]-ceph-3-eme-4-carboxylic acid Using the procedure of Example 9, 1 g of the product of Step A was reacted to the removal of methylene chloride and addition of water and 40 ml of aqueous half-saturated sodium chloride solution were added thereto. The mixture was extracted with methyl acetate and the organic phase was dried and evaporated to dryness under reduced pressure. The oily residue was taken up in 50 ml of aqueous saturated sodium chloride solution and the mixture was triturated and vacuum filtered. The product was rinsed with water and then ether to obtain 0.602 g of syn isomer of 3-(isopropoxymethyl-7-[2-(2-amino-4-thiazolyl)-2-methoxyimino-acetamido]-ceph-3-eme-4-carboxylic acid. The wash waters were extracted with methyl acetate and the organic phase was dried and evaporated to dryness under reduced pressure. The residue was taken up in 50 ml of ether and vacuum filtered to obtain 0.686 g of the desired product.

UV Spectrum (ethanol): Max. at 236 nm $E_1^1=359$; $\epsilon=16,400$; Inflex. towards 252 nm $E_1^1=318$; $\epsilon=14,500$; Inflex. towards 291 nm $E_1^1=151$.

UV Spectrum (0.1N HCl-ethanol): Max. at 263 nm $E_1^1=385$; $\epsilon=17,500$.

NMR Spectrum (DMSO): Peaks at 1.03-1.15 ppm (hydrogens of

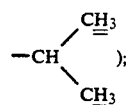

at ~3.57 ppm (—CH$_2$S—); at 4.23 ppm (hydrogens of OCH$_2$—); at 3.88 ppm (hydrogens of —N—O—CH$_3$); at 5.12-5.2 ppm (6-hydrogen); at 5.65-5.73 ppm and 5.78-5.87 ppm (7-hydrogen); at 6.82 ppm (5-hydrogen of thiazole); at ~9.58-9.72 ppm (—NHCO—).

EXAMPLE 13

Syn isomer of 3-benzyloxymethyl-7-[2-(2-amino-4-thiazolyl)-2-methoxyimino-acetamido]-ceph-3-eme-4-carboxylic acid

STEP A:
3-benzyloxy-7-amino-ceph-3-eme-4-carboxylic acid

Using the procedure of Step A of Example 8, 27.2 g of 7-amino-cephalosporanic acid, 128 ml of the etherate of boron trifluoride, 126 ml of benzyl alcohol and 90 ml of triethylamine were reacted to obtain 27.1 g of raw product. 25 g of the said product and 250 ml of acetic acid were added to 25 ml of the etherate of boron trifluoride followed by the addition of 25 ml of triethylamine which caused precipitation. The mixture was vacuum filtered and the product was rinsed with acetic acid, acetone and then ether to obtain 4.6 of product. 4.8 g of the said product were dissolved at 45° C. in 20 ml of 2N hydrochloric acid and 8 ml of concentrated hydrochloric acid and the solution was treated with activated carbon. 6 ml of ammonium hydroxide were added to the mixture which was then vacuum filtered. The product was rinsed with water, acetone and then ether to obtain 2 g of 3-benzyloxy-7-amino-ceph-3-eme-4-carboxylic acid.

UV Spectrum (0.1N HCl-ethanol): Max. at 259 nm $E_1^1=216$; $\epsilon=6,900$.

NMR Spectrum (DMSO): Peaks at 4.28 and 4.45 ppm (—CH$_2$O—CH$_2$—); at 4.73-4.82 ppm and 4.95-5.03 ppm (6- and 7-hydrogens); at 7.33 ppm (aromatic).

Step B: Syn isomer of 3-benzyloxymethyl-7-[2-amino-4-thiazolyl)-2-methoxyimino-acetamido]-ceph-3-eme-4-carboxylic acid Using the procedure of Example 9, 1.175 g of the product of Step A were reacted up to the removal of methylene chloride and addition of water. An aqueous saturated sodium chloride solution was added to the mixture which was then vacuumed filtered. The product was rinsed with water and then with either to obtain 0.905 g and then 0.590 g of product. 0.707 g of the product were dissolved in 7 ml of water and 0.2 ml of triethylamine and the solution was treated with activated carbon 0.15 ml of 50% aqueous formic acid were added to the mixture which was vacuum filtered to obtain 0.484 g of product which together with the 0.590 g of product was triturated in 10 ml of 50% aqueous ethanol containing 0.6 ml of formic acid. The mixture stood at 20° C. for 15 minutes and was vacuumed filtered. 1.6 ml of ammonium hydroxide and 20 ml of water were added to the filtrate and the mixture was extracted with methyl acetate. The organic phase was washed with water, dried and evaporated to dryness under reduced pressure. The residue was triturated with 10 ml of ethanol and the mixture was vacuum filtered. The product was rinsed with ethanol and then with ether to obtain 0.283 g of syn isomer of 3-benzyloxymethyl-7-[2-(2-amino-4-thiazolyl)-2-methoxyimino-acetamido]-ceph-3-eme-4-carboxylic acid.

UV Spectrum (ethanol): Max. at 237 nm $E_1^1 350$; $\epsilon = 17,700$; Inflex. towards 255 nm $E_1^1 = 308$; Inflex. towards 290 nm $E_1^1 = 154$;

UV Spectrum (0.1N HCl-ethanol): Max. at 262 nm $E_1^1 = 367$; $\epsilon = 18,500$.

NMR Spectrum (DMSO): Peaks at 3.85 ppm (hydrogens of N—OCH$_3$); at 4.31 ppm (hydrogens of —CH$_2$O—); at 4.45 ppm (hydrogens of —O—CH$_2\phi$); at 5.12–5.2 ppm (6-hydrogen); at 5.68–5.77 ppm and 5.82–5.9 ppm (7-hydrogen); at 6.75 ppm (5-hydrogen of thiazole); at 7.33 ppm (phenyl); at ~9.52–9.65 ppm (NHCO).

EXAMPLE 14

Syn isomer of 3-(2-methoxyethoxy)-methyl-7-[2-(2-amino-4-thiazolyl)-2-methoxyimino-acetamido]-ceph-3-eme-4-carboxylic acid

Step A:
3-(2-methoxyethoxy)-methyl-7-amino-ceph-3-eme-4-carboxylic acid

Using the procedure of Step A of Example 8, 27.2 g of 7-amino-cephalosporanic acid, 170 ml of the etherate of boron trifluoride, 136 ml of 3-methoxy-ethanol and 125 ml of triethylamine were reacted to obtain 19.25 g of raw product. A mixture of 17 g of the said product, 170 ml of methylene chloride and 8.3 ml of triethylamine was stirred for 20 minutes and was vacuumed filtered. The 9.28 g of dried product were taken up in 130 ml of acetone containing 2% of water and 4.5 of triethylamine and the mixture was stirred for 15 minutes and was then filtered. The product was rinsed with acetone and then with ether to obtain 6.35 g of product which was treated in the same fashion to obtain 5.77 g of 3-(2-methoxyethoxy)-methyl-7-amino-ceph-3-eme-4-carboxylic acid.

UV Spectrum (0.1N HCl-ethanol): Max. at 260–261 nm $E_1^1 = 226$; $\epsilon = 6,500$; Inflex. towards 330 nm $E_1^1 = 9$.

NMR Spectrum (DMSO): Peaks at 3.23 ppm (OCH$_3$); at 3.45 ppm (—CH$_2$—S and —O—CH$_2$—CH$_2$—O—); at 4.23 ppm (—CH$_2$O—); at 4.7–4.77 ppm and 4.92–5 ppm (6- and 7-hydrogens).

Step B: Syn isomer of 3-(2-methoxyethoxy)-methyl-7-[2-(2-amino-4-thiazolyl)-2-methoxyimino-acetamido]-ceph-3-eme-4-carboxylic acid Using the procedure of Example 9, 1.160 g of the product of Step A were reacted up to the methylene chloride removal and water addition and then 50 ml of aqueous saturated sodium chloride solution were added. The mixture was vacuum filtered and the filtrate was extracted with methyl acetate. The organic phase was washed with water, dried and evaporated to dryness under reduced pressure and the residue was taken up in 50 ml of aqueous saturated sodium chloride solution. The decanted liquid phase was extracted with methyl acetate and the organic phase was washed with water, dried and evaporated to dryness under reduced pressure at less than 30° C. The residue was triturated with 20 ml of ether and was vacuum filtered to obtain 0.725 g of raw product. 0.720 g of the latter were taken up in 15 ml of water and the mixture was stirred at 20° C. for 5 minutes and was vacuum filtered. The filtrate was extracted with methyl acetate and the organic phase was washed with water, dried and evaporated to dryness under reduced pressure. The residue was triturated with 20 ml of ether and was vacuum filtered to obtain 0.500 g of syn isomer of 3-(2-methoxyethoxy)-methyl-7-[2-(2-amino-4-thiazolyl)-2-methoxyimino-acetamido]-ceph-3-eme-4-carboxylic acid.

UV Spectrum (ethanol): Max. at 238 nm $E_1^1 = 342$; $\epsilon = 16,000$; Inflex. towards 250 nm $E_1^1 = 313$; Inflex. towards 290 nm $E_1^1 = 141$.

UV Spectrum (0.1N HCl-ethanol): Max. at 265 nm $E_1^1 = 369$; $\epsilon = 17,400$.

NMR Spectrum (DMSO): Peaks at 3.23 ppm (OCH$_3$); at 3.45 ppm (—OCH$_2$—CH$_2$—O—); at 3.83 ppm (NOCH$_3$); at 4.28 ppm (—CH$_2$O—); at 5.11–5.17 ppm (6-hydrogen); at 5.69–5.74 ppm and 5.77–5.83 ppm (7-hydrogen); at 6.74 ppm (5-hydrogen of thiazole); at 7.22 ppm (NH$_2$); at 9.5–9.6 ppm (NHCO).

EXAMPLE 15

Syn isomer 3-methoxymethyl-S-oxido-7-[2-(2-amino-4-thiazolyl)-2-hydroxyimino-acetamido]-ceph-3-eme-4-carboxylic acid

Step A: Syn isomer of 3-methoxymethyl-S-oxido-7-[2-(2-tritylamino-4-thiazolyl)-2-{(1 1-methoxy)-ethoxyimino}-acetamido]-ceph-3-eme-4-carboxylic acid 1.45 g of the syn isomer of 3-methoxymethyl-7-[2-(2-tritylamino-4-thiazolyl)-2-(1-methyl-1-methoxy)-ethoxyimino-acetamido]-ceph-3-eme-4-carboxylic acid were dissolved at room temperature in 14 ml of methylene chloride and after cooling the mixture to −20° C., 440 mg of m-chloro-perbenzoic acid were added thereto. The mixture was stirred for 15 minutes and the temperature was allowed to rise to room temperature. 10 ml of isopropyl ether were added to the mixture and the methylene chloride was distilled. Another 10 ml of isopropyl ether were added thereto and the mixture was vacuum filtered to obtain 1.47 g of raw syn isomer of 3-methoxymethyl-S-oxido-7-[2-(2-tritylamino-4-thiazolyl)-2-{(1-methyl-1-methoxy)-ethoxyimino}-acetamido]-ceph-3-eme-4-carboxylic acid.

Step B: Syn isomer of 3-methoxymethyl-S-oxido-7-[2-(2-amino-4-thiazolyl)-2-hydroxyimino-acetamido]-ceph-3-eme-4-carboxylic acid 50 ml of ether were added to a mixture of 1.47 g of the product of Step A and 5 ml of a 66% aqueous formic acid solution and the mixture was vacuum filtered. The 0.785 g of product was taken up in 1 ml of water and 2 drops of pyridine and 10 ml of ethanol were added to the mixture which was vacuumed filtered. The product was rinsed with ethanol and then with ether to obtain 0.51 g of syn isomer of 3-methoxy-methyl-S-oxido-7-[2-(2-amino-4-thiazolyl)-2-hydroximino-acetamido]-ceph-3-eme-4-carboxylic acid.

UV Spectrum (0.1N HCl-ethanol): Inflex. towards 218 nm $E_1^1 = 303$; Max. at 261 nm $E_1^1 = 423$; $\epsilon 18,200$; Inflex. towards 375 nm $E_1^1 = 2$.

NMR Spectrum (DMSO): Peaks at 3.25 ppm (OCH$_3$); at 4.3–4.5 ppm and 4.4.21 ppm (—CH$_2$O—); at 4.98–5.06 ppm (6-hydrogen); at 6.83 ppm (5-hydrogen of thiazole); at 5.95–5.98 ppm and 6.05–6.13 ppm (7-hydrogen).

EXAMPLE 16

Syn isomer of 3-methylsulfinylmethyl-S-oxido-7-[2-(2-amino-4-thiazolyl)-2-hydroxyimino-acetamido]-ceph-3-eme-4-carboxylic acid Using the procedure of Example 15, 0.744 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and 0.404 g of m-chloro-perbenzoic acid were reacted to obtain 0.250 g of syn isomer of 3-methylsulfinylmethyl-S-oxido-7-[2-(2-amino-4-thiazolyl)-2-hydroxyimino-acetamido]-ceph-3-eme-4-carboxylic acid.

UV Spectrum (0.1N HCl-ethanol): Max. at 269 nm $E_1^1 = 396$; $\epsilon = 18,300$.

NMR Spectrum (DMSO): Peaks at 2.6 ppm ($CH_3$—SO); at 5–5.08 ppm (6-hydrogen); at 5.88–5.96 ppm and 6.03–6.12 ppm (7-hydrogen); at 6.78 ppm (5-hydrogen of thiazole).

EXAMPLE 17

Syn isomer of 3-methylthiomethyl-7-[2-(2-amino-4-thiazolyl)-2-benzyloxyimino-acetamido]-ceph-3-eme-4-carboxylic acid

Step A: Ethyl 2-(2-tritylamino-4-thiazolyl)-2-benzyloxyimino-carboxylate 23 ml of benzyl chloride were added over 5 minutes at 0° C. to a mixture of 9.88 g of ethyl 2-(2-tritylamino-4-thiazolyl)- 2-hydroxyimino-carboxylate hydrochloride (described in French Patent No. 2,383,188), 50 ml of dimethylformamide and 13.8 g of potassium carbonate and the mixture was stirred at room temperature for 20 hours. 500 ml of water and 100 ml of ethyl acetate were added to the mixture and the decanted organic phase was washed with water, dried and evaporated to dryness under reduced pressure. The residue was chromatographed over silica gel and was eluted with a 9-1 cyclohexane-ethyl acetate mixture to obtain 5.51 g of ethyl 2-(2-tritylamino-4-thiazolyl)-2-benzyloxyimino-carboxylate.

Step B: Syn isomer of 2-(2-tritylamino-4-thiazolyl)-2-benyzloxyimino-acetic acid A mixture of 5.3 g of the product of Step A, 30 ml of ethanol, 8 ml of dioxane and 4.8 ml of 2N sodium hydroxide solution was stirred at room temperature for 20 hours and was then vacuum filtered. The product was rinsed with a 4-1 ethanol-dioxane mixture and then with ether to obtain 4.452 g of sodium salt. The latter was added to 50 ml of water, 50 ml of methylene chloride and 6 ml of 2N hydrochloric acid and the decanted organic phase was washed with water, dried and evaporated to dryness under reduced pressure. The residue was taken up in isopropyl ether, vacuum filtered and dried to obtain 3.708 g of 2-(2-tritylamino-4-thiazolyl)-2-benzyloxyimino-acetic acid melting at ≃153° C.

NMR Spectrum (deuterochloroform): Peaks at 7.3 ppm ($\phi s$); at 6.5 ppm (5-hydrogen of thiazole); at 5.25 ppm ($CH_2$—$\phi$).

Step C.: Mixed anhydride of p-toluene sulfonic acid and the syn isomer of 2-(2-tritylamino-4-thiazolyl)-2-benzyloxyimino-acetic acid 0.95 g of tosyl chloride and 0.7 ml of triethylamine were added at 0° C. to a mixture of 2.6 g of the product of Step B and 26 ml of acetone and the temperature was allowed to rise to room temperature. The mixture was stirred for one hour to obrain a suspension of mixed anhydride of p-toluene sulfonic acid and the syn isomer of 2-(2-tritylamino-4-thiazolyl)-2-benzyloxyimino-acetic acid which was used as is for the next step.

Step D: Syn isomer of 3-methylthiomethyl-7-[2-(2-tritylamino-4-thiazolyl)-2-benzyl oxyimino-acetamido]-ceph-3-eme-4-carboxylic acid.

The suspension of Step C was poured into previously cooled solution of 1.3 g of 3-methylthiomethyl-7-amino-ceph-3-eme-4-carboxylic acid, 1.4 ml of triethylamine and 13 ml of methylene chloride and the mixture was stirred at room temperature for 45 minutes. 0.7 ml of acetic acid were added to the mixture which was then evaporated to dryness under reduced pressure. The residue was taken up in a mixture of 40 ml of methylene chloride and 40 ml of 0.1N hydrochloric acid and the decanted organic phase was washed with water, dried and evaporated to dryness under reduced pressure to obtain 4.44 g of syn isomer of 3-methylthiomethyl-7-[2-(2-tritylamino-4-thiazolyl)-2-benzyloxyimino-acetamido]-ceph-3-eme-4-carboxylic acid.

Step E: Syn isomer of 3-methylthiomethyl-7-[2-(2-amino-4-thiazolyl-2-benzyloxyimino-acetamido]-ceph-3-eme-4-carboxylic acid The product of Step D was taken up in 22 ml of 67% aqueous formic acid and the mixture was stirred for 45 minutes at 45° C. 10 of water were added to the mixture which was then filtered and the filtrate was evaporated to dryness under reduced pressure at 35° C. The residue was taken up in 50% aqueous ethanol and then with water and vacuum filtered. The product was dried under reduced pressure to obtain 2.28 g of raw product which was chromatographed over silica gel and was eluted with aqueous 3M sodium clhoride solution containing 4% of sodium bicarbonate. The organic phase was acidified with N hydrochloric acid and was vacuum filtered. The product was empasted with water and dried to obtain 0.911 g of product. The latter was taken up in 8 ml of methylene chloride containing 10% of methanol and a little magnesium sulfate was added thereto. The mixture was vacuum filtered and the filtrate was evaporated to dryness under reduced pressure. The residue was taken up in either and was vacuum filtered. The product was dried to obtain 0.686 g of pure syn isomer of 3-methyl-thiomethyl-7-[2-(2-amino-4-thiazolyl)-2-benzyloxyimino-acetamido]-ceph-3-eme-4-carboxylic acid melting at 168° C. (decomposition).

UV Spectrum (ethanol): Max. at 236 nm: $\epsilon = 18,100$; Inflex. towards 257 nm; Inflex. towards 301 nm: $\epsilon = 6,700$.

UV Spectrum (0.1N HCl-ethanol): Max. at 266 nm: $\epsilon = 18,800$.

NMR Spectrum (DMSO): Peaks at 1.92 ppm (—SC-$H_3$—); at 3 to 4.16 ppm (—$CH_2$—S); at 6.8 ppm (5-hydrogen of thiazole); at 7.41 ppm (hydrogen of phenyl); at 5.2 ppm (hydrogens of —$CH_2\phi$).

EXAMPLE 18

Syn isomer of 3-methylthiomethyl-7-[2-(2-amino-4-thiazolyl)-2-{2-bromoethoxyimino}-acetamido]-ceph-3-eme-4-carboxylic acid Using the procedure of Example 17, 1.909 g of the syn isomer of 2-(2-tritylamino-4-thiazolyl)-2-(2-bromoethoxyimino)-acetic acid (described in French Patent No. 2,438,050), 0.68 g of tosyl chloride, 0.927 g of 3-methylthiomethyl-7-amino-ceph-3-eme-4-carboxylic acid and 15 ml of 67% aqueous formic acid were reacted to obtain 0.615 g of pure syn isomer of 3-methylthiomethyl-7-[2-(2-amino-4-thiazolyl)-2-{2-bromoethoxyimino}-acetamido]-ceph-3-eme-4-carboxylic acid with a melting point of 185° C. (decomposition).

UV Spectrum (ethanol): Max. at 232 nm: $\epsilon = 18,000$; Inflex. towards 255 nm; Inflex. towards 296 nm: $\epsilon = 7,600$.

UV Spectrum (0.1N HCl-ethanol): Max. at 265 nm: $\epsilon = 18,800$; Inflex. towards 280 nm.

NMR Spectrum (DMSO): Peaks at 2 ppm (—SCH$_3$); at 3.44 to 5.2 ppm (hydrogens of CH$_2$—CH$_2$Br and CH$_2$—SCH$_3$); at 4.32 to 4.45 ppm (hydrogens of CH$_2$CH$_2$Br); at 6.9 ppm (5-hydrogen of thiazole).

EXAMPLE 19

Syn isomer of 1-(1-oxopropoxy)-propyl 3-methylthiomethyl-7-[2-(2-amino-4-thiazolyl-2-hydroxyimino-acetamido]-ceph-3-eme-4-carboxylate

Step A: Bromopropyl propionate 26.4 ml of propionaldehyde were added over 25 minutes with stirring at 5° C. to a mixture of 180 mg of zinc chloride and 30 ml of propionyl bromide and the mixture was stirred at room temperature for 15 hours. The mixture was evaporated to dryness under reduced pressure to obtain 14.27 g of syn isomer of bromopropyl propionate which was used as is for the next step.

Step B: Syn isomer of 1-(1-oxopropoxy)-propyl 3-methylthio-methyl-7-[2-(2-tritylamino-4-thiazolyl)-{2-methyl-1-methoxy)-ethoxyimino)-acetamido]-ceph-3-eme-4-carboxylate 3 ml of the product of Step A were added dropwise under an inert atmosphere over 15 minutes to a mixture of 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 16.5 ml of dimethylformamide and 0.49 g of potassium carbonate and the mixture was poured into 200 ml of water. The mixture was extracted with ethyl acetate and the organic phase was washed with an aqueous saturated sodium chloride solution, dried and evaporated to dryness under reduced pressure at less than 40° C. to obrain 6.3 g of raw syn isomer of 1-(1-oxopropoxy)-propyl 3-methylthio-methyl-7-[2-(2-tritylamino-4-thiazolyl)-2-{(1-methyl-1-methoxy-ethoxyimino}-acetamido]-ceph-3-eme-4-carboxylate.

Step C: Syn isomer of 1-(1-oxopropoxy)-propyl 3-methyl thio-methyl thio-7-/2-(2-amino-4-thiazolyl)-2-hydroxyimino-acetamido/-ceph-3-eme-4-carboxylate A mixture of 6.3 g of the product of Step B and 53 ml of a 90% aqueous formic acid solution was stirred for one hour and was filtered and the filtrate was added to 500 ml of water. The mixture was stirred for 5 minutes and was extracted with ethyl acetate. The organic phase was washed with aqueous saturated sodium chloride solution, dried and evaporated to dryness under reduced pressure to obtain 2.66 g of product which was chromatographed over silica gel. Elution was with a 92-8 methylene chloride-methanol mixture and the organic phase was evaporated to dryness. The residue was dissolved in methanol and crystallized from isopropyl ether to obtain 1.11 g of syn isomer of 1-(1-oxopropoxy)-propyl 3-methyl thiomethyl thio-7-/2-(2-amino-4-thiazoyl)-2-hydroxyimino-acetamido/-ceph-3-eme-4-carboxylate melting at 140° C. (decomposition).

UV Spectrum (0.1N HCl-ethanol): Max. at 264 nm $E_1^1 = 347$; $\epsilon = 18,800$.

NMR Spectrum (deuterochloroform): Peaks at 2.06 ppm (—SCH$_3$); at 1.03 to 1.26 ppm and 2.21 to 2.56 ppm

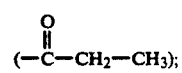

at 6.83–7.08 ppm (—COOCH—); at 0.85 to 1.83 ppm (—CH$_2$—CH$_3$).

EXAMPLE 20

Syn isomer of cyanomethyl 3-methylthiomethyl-7-[2-(2-amino-4-thiazolyl)-2-hydroxyimino-acetamido]-ceph-3-eme-4-carboxylate Using the procedure of Example 19, 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and 2.2 ml of acetonitrile bromide were reacted to obtain 0.767 g of syn isomer of cyanomethyl 3-methyl-thiomethyl-7-[2-(2-amino-4-thiazolyl)-2-hydroxyimino-acetamido]-ceph-3-eme-4-carboxylate which after crystallization from isopropyl ether melted at ~145° C.

UV Spectrum (0.1N HCl-ethanol): Max. at 265 nm $E_1^1 = 367$; $\epsilon = 17,200$.

NMR Spectrum (DMSO): Peaks at 2.01 ppm (—SCH$_3$); at 5.23 ppm (—COOCH$_2$—); at 6.75 ppm (5-hydrogen of thiazole).

EXAMPLE 21

Syn isomer of 1-(1-oxoethoxy)-propyl 3-methylthiomethyl-7-[2-(2-amino-4-thiazolyl)-2-hydroxyimino-acetamido]-ceph-3-eme-4-carboxylate.

Step A: 3-bromopropyl acetate 40 ml of propionaldehyde were added over 12 minutes at 15° C. to a mixture of 37 ml of acetyl bromide and 0.242 g of zinc chloride and the mixture was stirred at room temperature for 15 hours. The mixture was distilled at 53° to 58° C. at 80 to 90 mmHg and 5 ml of the product and 5 ml of chloroform were stirred at room temperature while adding 840 mg of hexamethylenetetraamine thereto in small fractions. The mixture was stirred for 10 minutes to obtain a solution of 3-bromo-propyl acetate which was used as is for the next step.

Step B: Syn isomer of 1-(1-oxoethoxy)-propyl 3-methylthio-methyl-7-[8-(2-amino-4-thiazolyl)-2-hydroxyimino-acetamido]-ceph-3-eme-4-carboxylate Using the procedure of Example 19, 5 g of the syn isomer of 3-methylthiomethyl-7-[2-(2-tritylamino-4- thiazolyl)-2-{(1-methyl-1-methoxy)-ethoxyimino}-acetamido]-ceph-3-eme-4-carboxylic acid and 7 ml of the solution of Step A were reacted to obtain 0.965 g of pure syn isomer of 1-(1-oxoethoxy)-propyl 3-methylthiomethyl-7-[2-(2-amino-4-thiazolyl)-2-hydroxyimino-acetamido]-ceph-3-eme-4-carboxylate melting at 130° C. (decomposition).

UV Spectrum (0.1N HCl-ethanol): Max. at 264 nm $E_1^1 = 347$; $\epsilon 18,400$.

NMR Spectrum (deuterochloroform): Peaks at 0.85 to 1.08 ppm (—CH$_2$—CH$_3$); at 1.88 to 1.93 ppm (—SCH$_3$ and

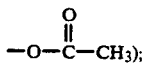

at 7.01 ppm (5-hydrogen of thiazole); at 6.83 to 7.16 ppm (COOCHO).

EXAMPLE 22

Syn isomer of 1-acetyloxy ethyl 3-methylthiomethyl-7-[2-(2-amino-4-thiazolyl)-2-hydroxyimino-acetamido]-ceph-3-eme-4-carboxylate Using the procedure of Example 19, 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and 1.55 ml of bromoethyl acetate were reacted to obtain 0.867 g of syn isomer of 1-acetyloxy ethyl 3-methylthiomethyl-7-[2-(2-amino-4-thiazolyl)-2-hydroxyimino-acetamido]-ceph-3-eme-4-carboxylate melting at ∼150° C. (decomposition).

UV Spectrum (0.1N HCl-ethanol): Max. at 265 nm $E_1^1 = 347$; $\epsilon = 17,800$.

MNR Spectrum (deuterochloroform): Peaks at 2.26–2.35 ppm (hydrogens of CH$_3$—CH$_2$); at 3.06–3.12 ppm (—SCH$_3$ and OAc); at 5.38 ppm (—CH$_2$—S—); at 10.4 ppm (5-hydrogen of thiazole).

EXAMPLE 23

Syn isomer of 2-chloro-2-propenyl 3-methylthiomethyl-7-[2-(2-amino-4-thiazolyl)-2-hydroxyimino-acetamido]-ceph-3-eme-4-carboxylate Step A: 3-iodo-2-chloro-1-propene A mixture of 6.1 ml of 2,3-chloro-1-propene, 10 g of sodium iodide and 43 ml of acetone was refluxed under an inert atmosphere for 40 minutes and the mixture was cooled to room temperature and was vacuum filtered to obtain a solution of 3-iodo-2-chloro-1-propene which was used as is for the next step.

Step B: Syn isomer of 2-chloro-2-propenyl 3-methylthiomethyl-7-[2-tritylamino-4-thiazolyl)-2-(1-methyl-1-1-methoxy)-ethoxyimino-acetamido]-ceph-3-eme-4-carboxylate The solution of Step A was added dropwise under an inert atmosphere to a solution of 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 16 ml of dimethylformamide and 0.477 g of potassium carbonate and after 30 minutes, the acetone was distilled under reduced pressure at less than 40° C. 250 ml of isopropyl ether were added to the mixture and the liquid phase was decanted. The residue was dried under reduced pressure to obtain 7.8 g of syn isomer of 2-chloro-2-propenyl 3-methyl-thiomethyl-7-[2-(2-tritylamino-4-thiazolyl)-2-{(1-methyl-1-methoxy)-ethoxyimino}-acetamido]-ceph-3-eme-4-carboxylate.

Step C: Syn isomer of 2-chloro-2-propenyl 3-methylthiomethyl-7-[2-(2-amino-4-thiazolyl)-2-hydroxyimino-acetamido]-ceph-3-eme-4-carboxylate Using the procedure of last step of Example 19, the 7.8 g of the product of Step B were reacted to obtain 1.18 g of syn isomer of 2-chloro-20-propenyl 3-methyl-thiomethyl-7-[2-(2-amino-4-thiazolyl)-2-hydroxyimino-acetamido]-ceph-3-eme-4-carboxylate melting at ∼146° C. (decomposition).

UV Spectrum (0.1N HCl-ethanol): Max. at 265 nm $E_1^1 = 377$; $\epsilon = 19,000$.

NMR Spectrum (deuterochloroform): Peaks at 2.03 ppm (SCH$_3$); at 3.63 ppm (—SCH$_2$—); at 4.83 to 5.6 ppm (CH$_2$= and —COOCH$_2$—); at 5.1–5.18 ppm (6-hydrogen).

EXAMPLE 24

Syn isomer of methylthiomethyl 3-methylthiomethyl-7-[2-(2-amino-4-thiazolyl)-2-hydroxyimino-acetamido]-ceph-3-eme-4-carboxylate STEP A; Syn isomer of methylthiomethyl 3-methylthiomethyl-7-[2-(2-tritylamino-4-thiazolyl)-2-{(1-methyl-1-methoxy)-ethoxyimino)-acetamido]-ceph-3-eme-4-carboxylate 3.4 ml of chloromethyl methyl sulfide were added dropwise under an inert atmosphere to a solution of 5 g of the syn isomer of 3-methylthiomethyl-7-[2-(2-tritylamino-4-thiazolyl)-2-}(1-methyl-1-methoxy)-ethoxyimino}-acetamido]-ceph-3-eme-4-carboxylic acid, 16 ml dimethylformamide and 480 mg of potassium carbonate and the mixture was stirred for 35 minutes and then poured into 200 ml of aqueous saturated sodium chloride solution. The mixture was vacuum filtered and the product was dissolved in chloroform. The solution was washed with aqueous saturated sodium chloride solution, dried and evaporated to dryness under reduced pressure at less than 40° C. The residue was taken up in petroleum ether (b.p. =60°–80° C.) to solidify the product to obtain 5.2 g of syn isomer of methylthiomethyl 3-methylthiomethyl-7-[2-(2-tritylamino-4-thiazolyl)-2-{(1-methyl-1-methoxy)-ethoxyimino}-acetamido]-ceph-3-eme-4-carboxylate which was used as is for the next step.

STEP B: Syn isomer of methylthiomethyl 3-methylthiomethyl-7-[2-(2-amino-4-thiazolyl)-2-hydroxyimino-acetamido]-ceph-3-eme-4-carboxylate A solution of 5.05 g of the product of Step A in 50 ml of methanol stood at room temperature for 3 days and was then evaporated to dryness under reduced pressure at less than 40° C. The residue was added to 15 ml of isopropyl ether and the mixture was stirred at room temperature for 20 minutes and was vacuum filtered. The product was rinsed with isopropyl ether and the 4.5 g of product was chromatographed over silica gel. The product was eluted with a 92–8 methylene chloride-methanol mixture and the eluant was evaporated to dryness. The residue was added to chloroform and isopropyl ether was added to the solution cause precipitation. The mixture was filtered and the product was dried to obtain 0.969 g of syn isomer of methylthiomethyl 3-methylthiomethyl-7-[2-(2-amino-4-thiazolyl)-2-hydroxyimino-acetamido]-ceph-3-eme-4-carboxylate melting at 140° C. (decomposition).

UV Spectrum (0.1N HCl-ethanol): Max. at 265 nm $E_1^1=379$; $\epsilon=18,600$.

NMR Spectrum (deuterochloroform): Peaks at 2.08 ppm (3-SCH$_3$); at 2.3 ppm (4-SCH$_3$); at 5.51 ppm (COOCH$_2$—S).

EXAMPLE 25

Syn isomer of 1-(2,2-dimethyl-1-oxopropoxy)-ethyl 3-methylthiomethyl-7-[2-(2-amino-4-thiazolyl)-2-hydroxyimino-acetamido]-ceph-3-eme-4-carboxylate

STEP A: 1-iodoethyl tert.-butylcarboxylate

A mixture of 61.4 ml of pivaloyl chloride and 250 mg of zinc chloride was stirred for 5 minutes and cooled to 15° C. after which 40 ml of acetaldehyde were added thereto over one hour. The mixture stood at room temperature for 15 hours and was evaporated to dryness under reduced pressure to obtain 29.01 g of 2-chloroethyl pivalate distilling at 56° to 58° C. at 27 mm Hg.

7.45 g of sodium iodide were slowly added to 20 ml of tetramethylene and after stirring the mixture for 10 minutes, 5 ml of 2-chloroethyl pivalate were added. The mixture was stirred for 30 minutes at 18° C. for a solution of 1-iodoethyl tert-.butyl-carboxylate.

STEP B: Syn isomer of 1-(2,2-dimethyl-1-oxopropoxy)-ethyl 3-methylthiomethyl-7-[2-(2-tritylamino-4-thiazolyl)-2-{(1-methyl-1-methoxy)-ethoxyimino}-acetamido]ceph-3-eme-4-carboxylate 3.72 g of the syn isomer of 3-methylthiomethyl-7-[2-(2-tritylamino-4-thiazolyl)-2-(1-methyl-1-methoxy)-ethoxyimino -acetamido]-ceph-3-eme-4-carboxylic acid were slowly added under an inert atmosphere to 7.5 ml of tetramethylene and then 0.375 g of potassium carbonate and then the product of Step A were added thereto. After one hour, 1.125 g of potassium carbonate were added thereto and the mixture was stirred for 10 minutes and poured into a mixture of 500 ml of water, 250 g of ice and 25 ml of 0.1N hydrochloric acid. The mixture was stirred for 15 minutes and was extracted with ethyl acetate. The organic phase was washed with water and then aqueous saturated sodium chloride solution, dried and evaporated to dryness under reduced pressure at less than 30° C. The 8.69 g of raw product were added to petroleum ether (b.p.=60°-80° C.) and was filtered to obtain 5.42 g of syn isomer of 1-(2,2-dimethyl-1-oxopropoxy)-ethyl 3-methylthiomethyl-7-[2-(2-tritylamino-4-thiazolyl)-2{(1-methyl-1-methoxy)-ethoxyimino}-acetamido]-ceph-3-eme-4-carboxylate.

STEP C: Syn isomer of 1-(2,2-dimethyl-1-oxopropoxy)-ethyl 3-methylthiomethyl-7-[2-(2-amino-4-thiazolyl)-2-hydroxyiminoacetamido]-ceph-3-eme-4-carboxylate The product of Step B was added to 55 ml of 88% aqueous formic acid and the mixture was stirred for 90 minutes and was filtered. The filtrate was poured into 650 ml of ice water and the mixture was extracted with chloroform. The organic phase was washed with water and with aqueous saturated sodium chloride solution, dried and evaporated to dryness under reduced pressure at less than 35° C. The 3.04 g of residue was chromatographed over silica gel and was eluted with a 98-2 methylene chloride-methanol mixture. The solution was evaporated to dryness and the residue was added to chloroform. Precipitation was induced by addition of isopropyl ether and the mixture was filtered. The product was dried to obtain 0.733 g of syn isomer of 1-(2,2-dimethyl-1-oxopropoxy)-ethyl 3-methylthiomethyl-7-[2-(2-amino-4-thiazolyl)-2-hydroxyimino-acetamido]-ceph-3-eme-4-carboxylate melting at ~140° C.

UV Spectrum (0.1N HCl-ethanol): Inflex. towards 219 nm $E_1^1=265$; Max. at 265 nm $E_1^1=337$; $\epsilon=18,800$.

NMR Spectrum (deuterochloroform): Peaks at 2.06 ppm (CH$_3$—S—); at 1.19-1.23 ppm (tert.-butyl); at 1.5-1.6 ppm (hydrogens of CH$_3$—CH—); at 3.33 ppm and 3.9 ppm (CH$_2$S).

EXAMPLE 26

Syn isomer of benzyl 3-methylthiomethyl-7-[2-(2-amino-4-thiazolyl)-2-hydroxyimino-acetamido]-ceph-3-eme-4-carboxylate

STEP A: Syn isomer of sodium 3-methylthiomethyl-7-[2-(2-amino-4-thiazolyl)-2-hydroxyimino-acetamido]-ceph-3-eme-4-carboxylate 3.5 ml of a methanolic solution of sodium acetate and 30 ml of ethanol were added to a solution of 1 g of the syn isomer of 3-methylthiomethyl-7-[2-(2-amino-4-thiazolyl)-2-hydroxyimino-acetamido]-ceph-3-eme-4-carboxylic acid in 2 ml of dimethylformamide and the mixture was vacuum filtered. The product was rinsed with ethanol and then with ether to obtain 0.804 g of syn isomer of sodium 3-methylthiomethyl-7-[2-(2-amino-4-thiazolyl)-2-hydroxyimino-acetamido]-ceph-3-eme-4-carboxylate.

STEP B: Syn isomer of benzyl 3-methylthiomethyl-7-[2-(2-amino-4-thiazolyl)-2-hydroxyimino-acetamido]-ceph-3-eme-4-carboxylate 0.21 ml of benzyl bromide was slowly added to a mixture of 0.84 g of the product of Step A and 4 ml of dimethylformamide and the mixture stood at room temperature for one hour. 40 ml of water were added thereto and the mixture was vacuum filtered. The product was rinsed with water, with isopropyl ether and dried to obtain 0.605 g of product. The latter was chromatographed over silica gel and was eluted with a 95-5 methylene chloride-methanol mixture. The product was crystallized from isopropyl ether to obtain 0.225 of pure syn isomer of benzyl 3-methylthiomethyl-7-[2-(2-amino-4-thiazolyl)-2-hydroxyimino-acetamido]-ceph-3-eme-4-carboxylate melting at 114° C.

UV Spectrum (0.1N HCl-ethanol): Max. at 263-264 nm: $\epsilon=19,400$.

NMR Spectrum (deuterochloroform): Peaks at 2.01 ppm (—SCH$_3$); at 7.08 ppm (5-hydrogen of thiazole); at 7.43 ppm (hydrogen of phenyl); at 5.3 ppm (hydrogens of COOCH$_2$—$\phi$).

EXAMPLE 27

Syn isomer of (1-oxohexadecanoxy)-methyl 3-methylthiomethyl-7-[2-(2-amino-4-thiazolyl)-2-hydroxyimino-acetamido]-ceph-3-eme-4-carboxylate

STEP A: Iodomethyl palmitate

A mixture of 33 ml of palmitoyl chloride, 3 g of paraformaldehyde and 50 mg of zinc chloride was heated at 80° C. under an inert atmosphere for 20 minutes and the mixture was then cooled to room temperature and was vacuum filtered. The product was dissolved in 10 ml of chloroform and 100 ml of ethanol were added thereto. The mixture was vacuum filtered to obtain 5 g of chloromethyl palmitate.

A mixture of 4.116 g of the latter product, 2.025 g of sodium iodide and 20 ml of acetone was refluxed under an inert atmosphere for 20 minutes and the mixture was cooled to room temperature and filtered to obtain an acetone solution of iodomethyl palmitate which was immediately used in the next step.

STEP B: Syn isomer of (1-oxohexadecanoxy)-methyl 3-methylthiomethyl-7-[2-(2-amino-4-thiazolyl)-2-hydroxyimino-acetamido]-ceph-3-eme-4-carboxylate Using the procedure of Example 19, 5 g of the syn isomer of 3-methylthiomethyl-7-/2-(2-tritylamino-4-thiazolyl)-2-/(1-methyl-1-methoxy)ethoxyimino-acetamido-ceph-3-eme-4-carboxylic acid and 20 ml of the solution of Step A were reacted to obtain 2.02 g of syn isomer of (1-oxohexadecanoxy)-methyl 3-methylthiomethyl-7-[2-(2-amino-4-thiazolyl)-2-hydroxyimino-acetamido]-ceph-3-eme-4-carboxylate which after crystallization from petroleum ether (b.p.=60°–80° C.) melted at 125° C.

UV Spectrum (0.1N HCl-ethanol): Max. at 264 nm $E_1^1 268$; $\epsilon = 18,700$.

NMR (deuterochloroform): Peaks at 0.89 ppm ($CH_3$ of ester); at 2.37 ppm ($CH_2$ of ester); at 2.04 ppm ($-SCH_3$).

EXAMPLE 28

Syn isomer of (2,2-dimethyl-1-oxopropoxy)-methyl 3-methylthiomethyl-7-[2-(2-amino-4-thiazolyl)-2-hydroxyimino-acetamido]-ceph-3-eme-4-carboxylate Using the procedure of Step B of Example 19, 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and an acetone solution of iodomethyl palmitate prepared as in Step A of Example 27 were reacted to obtain after admixture with isopropyl ether 4.1 g of raw product which was then reacted as in Step C of Example 19 to obtain 1.98 g of syn isomer of (2,2-dimethyl-1-oxopropoxy)-methyl 3-methylthiomethyl-7-[2-(2-amino-4-thiazolyl)-2-hydroxyimino-acetamido]-ceph-3-eme-4-carboxylate melting at 140° C.

UV Spectrum (0.1N HCl-ethanol): Max. at 264 nm $E_1^1 = 325$; $\epsilon = 17,700$.

NMR Spectrum (deuterochloroform): Peaks at 2.02 ppm ($CH_3$-S-); at 3.61 ppm ($-CH_2S-$); at 6.93 ppm (5-hydrogen of thiazole); at 1.24 ppm (tert.-butyl).

EXAMPLE 29

Syn isomer of 1-oxopentoxymethyl 3-methylthiomethyl-7-[2-(2-amino-4-thiazolyl)-2-hydroxyimino-acetamido]-ceph-3-eme-4-carboxylate STEP A: Iodomethyl n-valerate A mixture of 12 g of paraformaldehyde and 48.2 g of n-valeric acid chloride was stirred at 90° C. for 4 hours and 0.3 g of zinc chloride were added thereto. The mixture was distilled at 71.5°–73° C. at 20 mm Hg and 2.94 g of the recovered product were added to 2.25 g of sodium iodide and 15 ml of acetone. The mixture was refluxed for 20 minutes and was then cooled to room temperature and was vacuum filtered to obtain an acetone solution of iodomethyl n-valerate which was immediately used in the next step.

STEP B: Syn isomer of 1-oxopentoxymethyl 3-methylthiomethyl-7[2-(2-amino-4-thiazolyl)-2-hydroxyimino-acetamido]-ceph-3-eme-4-carboxylate Using the procedure of Step B of Example 19, the solution of Step A and 3.72 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid were reacted and the mixture was extracted with chloroform. The organic phase was washed with aqueous saturated sodium chloride solution and evaporated to dryness. The residue was added to petroleum ether (b.p.=60°–80° C.) and the mixture was evaporated to dryness. The residue was admixed with petroleum ether to obtain 4.8 g of the syn isomer of 1-oxopentoxymethyl 3-methylthiomethyl-7-[2-(2-tritylamino-4-thiazolyl)-2-{(1-methyl-1-methoxy)-ethoxyimino}-acetamido]-ceph-3-eme-4-carboxylate.

4.7 g of the said product were reacted according to Step C of Example 19 with 28.2 ml of a 90% aqueous formic acid solution and after extraction with chloroform and crystallization from isopropyl ether, 0.6 g of syn isomer of 1-oxopentoxymethyl 3-methylthiomethyl-7-[2-(2-amino-4-thiazolyl)-2-hydroxyimino-acetamido]-ceph-3-eme-4-carboxylate melting at ~158° C. were obtained.

UV Spectrum (0.1N HCl-ethanol): Max. at 265 nm $E_1^1 = 360$; $\epsilon = 19,600$.

NMR Spectrum (deuterochloroform): Peaks at 2.03 ppm ($-SCH_3$); at 0.82 to 0.97 ppm (hydrogens of $CH_3-CH_2$); at 2.3 to 2.46 ppm ($-COCH_2-$); at 6.96 ppm (5-hydrogen of thiazole).

EXAMPLE 30

Syn isomer of 1-oxobutoxymethyl 3-methylthiomethyl-7-[2-(2-amino-4-thiazolyl)-2-hydroxyimino-acetamido]-ceph-3-eme-4-carboxylate STEP A: Iodomethyl n-butyrate A mixture of 12 g of paraformaldehyde and 42.6 g of n-butyryl chloride and 1 g of zinc chloride was stirred at room temperature for 3 hours and at 90° C. for 4 hours and was distilled at 180–190 mm Hg to recover the fraction boiling at 104°–107° C. 2.8 g of the said product were slowly added to a mixture of 6 ml of tetramethylurea and 3.4 g of sodium iodide and the mixture was stirred for 2 hours and vacuum filtered to obtain a solution of iodomethyl n-butyrate which was immediately used in the next step.

STEP B: Syn isomer of 1-oxobutoxymethyl 3-methylthiomethyl-7-[2-(2-amino-4-thiazolyl)-2-hydroxyimino-acetamido]-ceph-3-eme-4-carboxylate Using the procedure of Step B of Example 25, 3.72 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and the solution of Step A were reacted to obtain 4.52 g of product which was then reacted with 45 ml of 90% aqueous formic acid by the method of Step C of Example 25 to obtain 0.627 g of syn isomer of 1-oxobutoxymethyl 3-methylthiomethyl-7-[2-(2-amino-4-thiazolyl)-2-hydroxyimino-acetamido]-ceph-3-eme-4-carboxylate melting at 160° C. (decomposition).

UV Spectrum (0.1N HCl-ethanol): Inflex. towards 261 nm $E_1^1 = 290$; $\epsilon = 15,300$; Max. at 264 nm $E_1^1 = 355$; $\epsilon = 18,800$.

NMR Spectrum (deuterochloroform): Peaks at 0.86 to 1.02 ppm ($CH_3$ of propyl); at 2.27 to 2.43 ppm ($COCH_2$—); at 5.88 ppm (—$COOCH_2O$); at 6.94 ppm (5-hydrogen of thiazole).

EXAMPLE 31

Syn isomer of acetyloxymethyl 3-methylthiomethyl-7-[2-(2-amino-4-thiazolyl)-2-hydroxyimino-acetamido]-ceph-3-eme-4-carboxylate Using the procedure of Example 19, 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and 20 ml of an acetone solution of iodomethyl acetate prepared extemporaneously from 1.92 g of chloromethyl acetate and 2.67 g of sodium iodide were reacted and the product was chromatographed over silica gel. Residual formic acid was removed by entrainment with nitromethane to obtain 1.677 g of pure syn isomer of acetyloxymethyl 3-methyl-thiomethyl-7-[2-(2-amino-4-thiazolyl)-2-hydroxyimino-acetamido]-ceph-3-eme-4-carboxylate melting at ~120° C. (decomposition).

UV Spectrum (0.1N HCl-ethanol): Max. at 263 nm $E_1^1 = 354$; $\epsilon = 17,800$.

NMR Spectrum (DMSO): Peaks at 2 ppm ($CH_3S$—); at 2.04 ppm (OAc); at 5.86 ppm ($COOCH_2O$); at 6.72 ppm (5-hydrogen of thiazole).

EXAMPLE 32

Syn isomer of 3,3-dimethyl-2-oxobutyl 3-methylthiomethyl-7-[2-(2-amino-4-thiazolyl)-2-hydroxyimino-acetamido]-ceph-3-eme-4-carboxylate Using the procedure of Step A of Example 25, 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 0.47 g of potassium carbonate, 27 ml of tetramethylurea and 0.95 ml of bromopinacolone were reacted to obtain 7.5 g of the syn isomer of 3,3-dimethyl-2-oxobutyl 3-methylthiomethyl-7-[2-(2-tritylamino-4-thiazolyl)-2-{(1-methyl-1-methoxy)-ethoxyimino}-acetamido]-ceph-3-eme-4-carboxylate.

Using the procedure of Step C of Example 25, the 7.5 g of the latter product and 53 ml of 90% aqueous formic acid were reacted and after purification by chromatography, residual formic acid was removed by entrainment with nitromethane to obtain 1.392 g of syn isomer of 3,3-dimethyl-2-oxobutyl 3-methylthiomethyl-7-[2-(2-amino-4-thiazolyl)-2-hydroxyimino-acetamido]-ceph-3-eme-4-carboxylate melting at ~160° C. (decomposition).

UV Spectrum (0.1N HCl-ethanol): Max. at 264 nm $E_1^1 = 388$; $\epsilon = 20,500$.

NMR Spectrum (deuterochloroform): Peaks at 1.23 ppm (tert.-butyl); at 4.82–5.1 ppm and 5.13–5.41 ppm ($COOCH_2CO$).

EXAMPLE 33

Syn isomer of 1-(1-oxopropoxy)-ethyl 3-methylthiomethyl-7-[2-(2-amino-4-thiazolyl)-2-hydroxyimino-acetamido]-ceph-3-eme-4-carboxylate A mixture of 9 ml of propionyl bromide and 50 mg of zinc chloride was cooled under reduced pressure at −15° C. and 5.4 ml of acetaldehyde were added thereto dropwise. The temperature was allowed to rise to room temperature to obtain 5.4 ml of a solution of bromoethyl propionate. Using the procedure of Example 19, the said solution and 10 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid were reacted. The resulting product was treated with formic acid and entrainment with nitromethane removed residual formic acid. The 1.5 g of product was chromatographed over silica gel and was eluted with a 92.5–7.5 methylene chloride-methanol mixture to obtain 0.566 g of pure syn isomer of 1-(1-oxopropoxy)-ethyl 3-methylthiomethyl-7-[2-(2-amino-4-thiazolyl)-2-hydroxyimino-acetamido]-ceph-3-eme-4-carboxylate melting at ~130° C.

UV Spectrum (0.1N HCl-ethanol): Max. at 264 nm $E_1^1 = 364$; $\epsilon = 19,300$.

NMR Spectrum (deuterochloroform): Peaks at 1.5–1.6 ppm (hydrogens of $CH_3$—CH); at 7.05 ppm (5-hydrogen of thiazole).

EXAMPLE 34

Syn isomer of 1-(1-oxobutoxy)-ethyl 3methylthiomethyl-7-[2-(2-amino-4-thiazolyl)-2-hydroxyimino-acetamido]-ceph-3-eme-4-carboxylate

STEP A: Iodoethyl butyrate

A mixture of 52 ml of butyryl chloride and 31 ml of acetaldehyde were placed in a flask at 16° C. under an inert atmosphere and 0.11 g of ferric chloride were added. The flask was hermetically sealed and the mixture stood at room temperature for 18 hours and was then poured into 200 ml of petroleum ether (b.p.=60°–80° C.). The mixture was treated with activated carbon and filtered and the filtrate was evaporated to dryness under reduced pressure at less than 30° C. to obtain chloroethyl butyrate as the fraction distilling between 64° to 68° C. at 34 mmHg.

4 g of sodium iodide were added piecemeal to a mixture of 4 g of the said product in 16 ml of dimethylacetamide and the mixture was stirred for 15 minutes to obtain a solution of iodoethyl butyrate which was immediately used in the next step.

STEP B: Syn isomer of 1-(1-oxo-butoxy)-ethyl 3-methylthiomethyl-7-[2-(2-amino-4-thiazolyl)-2-hydroxyimino-acetamido]-ceph-3-eme-4-carboxylate Using the procedure of Example 19, 5 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid in dimethylacetamide instead of dimethylformamide and the solution of Step A were reacted and the product was purified by chromatography. Residual formic acid was removed by entrainment with nitromethane to obtain 0.530 g of pure syn isomer of 1-(1-oxo-butoxy)-ethyl 3-methylthiomethyl-7[2-(2-amino-4-thiazolyl)-2-hydroxyimino-acetamido]-ceph-3-eme-4-carboxylate melting at 127° C.

UV Spectrum (0.1N HCl-ethanol): Max. at 264 nm $E_1^1 = 353$; $\epsilon = 19,200$.

NMR Spectrum (deuterochloroform): Peaks at 0.87 to 1.03 ppm (hydrogens of $CH_3$—$CH_2$—$CH_2$—); at 1.54–1.6 ppm (hydrogens of $CH_3$—CH=); at 2.09 ppm (hydrogens of $CH_3S$—); at 7.08 ppm (5-hydrogen of thiazole).

EXAMPLE 35

Syn isomer of 1-(1-oxohexadecyloxy)-ethyl 3-methylthiomethyl-7-[2-(2-amino-4-thiazolyl)-2-hydroxyimino-acetamido]-ceph-3-eme-4-carboxylate Using the procedure of Example 25, 744 mg of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 1.5 ml of tetramethylurea, 78 mg of potassium carbonate and an extemporaneously made solution of iodoethyl palmitate in tetramethylurea were reacted and then another 210 mg of potassium carbonate were added thereto. The mixture was extracted with chloroform which was distilled to dryness. The residue was taken up in 45 ml of 98% aqueous formic acid and the mixture was extracted with chloroform. The organic phase was evaporated to dryness and the residue was treated with petroleum ether (b.p. = 60°-80° C.) to obtain 0.353 g of syn isomer of 1-(1-oxohexadecyloxy)-ethyl 3-methylthiomethyl-7-[2-(2-amino-4-thiazolyl)-2-hydroxyimino-acetamido]-ceph-3-eme-4-carboxylate melting at 108° C.

UV Spectrum (0.1N HCl-ethanol): Inflex. towards 218 nm $E_1^1 = 215$; Max. at 265 nm $E_1^1 = 266$; $\epsilon = 18,900$.

NMR Spectrum (deuterochloroform): Peaks at 0.88 ppm ($CH_3$—$CH_2$—$CH_2$—); at 1.5-1.6 ppm (hydrogens of $CH_3CH=$); at 2.06 ppm (hydrogens of $CH_3S$—); at 3.63 ppm (—$CH_2$—S—).

EXAMPLE 36

Syn isomer of 2-propenyl 3-methylthiomethyl-7-[2-(2-amino-4-thiazolyl)-2-hydroxyimino-acetamido]-ceph-3-eme-4-carboxylate Using the procedure of Example 19, 3.72 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid in dimethylacetamide in place of dimethylformamide and 1.85 ml of allyl chloride were reacted to obtain 1.128 g of pure syn isomer of 2-propenyl 3-methylthiomethyl-7-[2-(2-amino-4-thiazolyl)-2-hydroxyimino-acetamido]-ceph-3-eme-4-carboxylate melting ~137° C. (decomposition).

UV Spectrum (0.1N HCl-ethanol): Max. at 262 nm $E_1^1 = 393$; $\epsilon = 18,500$.

NMR Spectrum (deuterochloroform): Peaks at 2.08 ppm ($CH_3S$—); at 4.73-4.83 ppm ($COOCH_2$—); at 5.08 to 6.5 ppm (—C=$CH_2$ and hydrogen of $\beta$-lactam); at 7.08 ppm (5-hydrogen of thiazole).

EXAMPLE 37

Syn isomer of 2,2-dimethylethyl 3-methylthiomethyl-7-[2-(2-amino-4-thiazolyl)-2-hydroxyimino-acetamido]-ceph-3-eme-4-carboxylate A mixture of 1.49 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 30 ml of ethyl acetate and 0.8 g of O-tert.-butyl-N,N'-diisopropylurea was heated to reflux and then was iced and vacuum filtered. The filtrate was evaporated to dryness under reduced pressure to obtain the syn isomer of 2,2-dimethylethyl 3-methylthiomethyl-7-[2-(2-tritylamino-4-thiazolyl)-2-{(1-methyl-1-methoxy)-ethoxyimino}-acetamido]-ceph-3-eme-4-carboxylate.

The said product was taken up in 7.5 ml of 67% aqueous formic acid and the mixture was stirred for 15 minutes at 45° C. 3 ml of water were added to the mixture which was vacuum filtered and the filtrate was evaporated to dryness under reduced pressure at 35° C. The residue was taken up in a 1-1 water-ethanol mixture and then water was added thereto. The product was dried to obtain 1.237 g of raw product which was chromatographed over silica gel. Elution with a 9-1 methylene chloride-methanol mixture yielded 0.47 g of pure syn isomer of 2,2-dimethylethyl 3-methylthiomethyl-7-[2-(2-amino-4-thiazolyl)-2-hydroxyimino-acetamido]-ceph-3-eme-4-carboxylate melting at 107° C. (decomposition).

UV Spectrum (ethanol): Max. at 223 nm: $\epsilon = 18,000$; Max. at 260 nm: $\epsilon = 13,500$.

UV Spectrum (0.1N HCl-ethanol): Inflex. towards 220 nm; Max. at 264 nm: $\epsilon = 18,600$.

NMR Spectrum (deuterochloroform): Peaks at 1.54 ppm (tert.-butyl); at 2.11 ppm (hydrogens of $CH_3S$—); at 7.08 ppm (5-hydrogen of thiazole).

EXAMPLE 38

Syn isomer of 2-methoxy-2-oxoethyl 3-methylthiomethyl-7-[2-(2-amino-4-thiazolyl)-2-hydroxyimino-acetamido]-ceph-3-eme-4-carboxylate A mixture of 1.6 ml of methyl monochloroacetate, 2.72 g of sodium iodide and 20 ml of acetone was refluxed under an inert atmosphere for 25 minutes and was then vacuum filtered to obtain a solution of iodomethyl acetate which was immediately used. Using the procedure of Example 19, 10 ml of the said solution and 3.44 g of the syn isomer of 3-methylthiomethyl-7-[2-(2-tritylamino-4-thiazolyl)-2-{(1-methyl-1-methoxy-ethoxyimino}-acetamido]-ceph-3-eme-4-carboxylic acid were reacted to obtain 2.8 g of 2-methoxy-2-oxoethyl 3-methylthiomethyl-7-[2-(2-tritylamino-4-thiazolyl)-2-{(1-methyl-1-methoxy)-ethoxyimino}-acetamido]-ceph-3-eme-4-carboxylate.

The said product was triturated at 60° C. for 10 minutes with 5.6 ml of pure formic acid and 16.8 ml of 50% aqueous formic acid and was then filtered. The filtrate was entrained with nitromethane to remove residual formic acid and was then dried and evaporated to dryness. The residue was taken up in chloroform and isopropyl ether was added to the solution to cause precipitation. The mixture was filtered and the product was dried to obtain 1.65 g of raw product which was added to a mixture of 90 ml of ethyl acetate and 90 ml of 0.1N hydrochloric acid. The mixture was extracted with ethyl acetate and the organic phases were evaporated to dryness. The residue was dissolved in chloroform and isopropyl ether was added to the solution to cause precipitation. The product was chromatographed over silica gel and was eluted with a 92.5-7.5 methylene chloride-methanol mixture to obtain 0.4 g of pure syn isomer of 2-methoxy-2-oxoethyl 3-methylthiomethyl-7-[2-(2-amino-4-thiazolyl)-2-hydroxyimino-acetamido]-ceph-3-eme-4-carboxylate melting at 156° C. (decomposition).

UV Spectrum (0.1N HCl-ethanol): Max. at 264 nm $E_1^1 = 383$; $\epsilon = 19,200$.

NMR Spectrum (deuterocholoroform): Peaks at 2.07 ppm (—$SCH_3$); at 3.68 ppm (—S—$CH_2$—); at 3.8 ppm (hydrogens of —$COOCH_3$); at 7 ppm (5-hydrogen of thiazole).

EXAMPLE 39

Syn isomer of 1-(acetyloxy)-ethyl 3-methylthiomethyl-7-[2-(2-amino-4-thiazolyl)-2-hydroxyimino-acetamido]-ceph-3-eme-4-carboxylate A mixture of 10.92 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 55 ml of dimethylformamide and 1.28 g of potassium carbonate was stirred at 20° C. for 15 minutes and after cooling the mixture to 5° C., 3.4 ml of 1-bromoethyl acetate were added thereto. The mixture was stirred for 20 minutes and then 0.1 g of potassium carbonate and 0.3 ml of 1-bromoethyl acetate were added thereto. The mixture was stirred for 25 minutes and 550 ml of water, 150 ml of ethyl acetate and 25 ml of 1M aqueous sodium bicarbonate solution were added thereto. The decanted aqueous phase was extracted with ethyl acetate and the organic phase was dried and evaporated to dryness under reduced pressure at less than 30° C. to obtain 14.3 g of the syn isomer of 1-(acetyloxy)-ethyl 3-methylthiomethyl-7-[2-(2-tritylamino-4-thiazolyl)-2-{(1-methyl-1-methoxy)-ethoxyimino}-acetamido]-ceph-3-eme-4-carboxylate.

A solution of 14.3 g of the said product in 61 ml of 66% aqueous formic acid was stirred at 50° C. for 10 minutes and 24 ml of water were added thereto. The mixture was filtered and the filtrate was evaporated to dryness under reduced pressure. The residue was taken up in a mixture of 50 ml of methylene chloride, 350 ml of water and 10 ml of aqueous sodium bicarbonate solution and was extracted with methylene chloride. The organic phase was washed with water, dried and evaporated to dryness. The residue was taken up in ethyl acetate and the mixture was vacuum filtered. The product was dried to obtain 4.87 g of syn isomer of 1-(acetyloxy)-ethyl 3-methylthiomethyl-7-[2-(2-amino-4-thiazolyl)-2-hydroxyimino-acetamido]-ceph-3-eme-4-carboxylate.

UV Spectrum (ethanol): Max. at 223 nm $E_1^1=387$; $\epsilon=19,300$; Max. at 259 nm $E_1^1=285$; $\epsilon=14,200$.

UV Spectrum (0.1N HCl-ethanol): Inflex. towards 219 nm $E_1^1=286$; Max. at 261-262 nm $E_1^1=390$; $\epsilon=19,500$.

NMR Spectrum (DMSO): Peaks at 1.43-1.51 ppm (hydrogens of $CH_3$—CH—); at 2.08 ppm (OAc); at 3.58 ppm (—$CH_2$—S); at 3.25 ppm ($OCH_3$); at 6.75 ppm (5-hydrogen of thiazole).

EXAMPLE 40

Syn isomer of 1-(1-oxoethoxy)-ethyl 3-ethoxymethyl-7-[2-(2-amino-4-thiazolyl)-2-hydroxyimino-acetamido]-ceph-3-eme-4-carboxylate Using the procedure of Example 39, 6 g of the syn isomer of 3-ethoxymethyl-7-[2-(2-tritylamino-4-thiazolyl)-2-{(1-methyl-1-methoxy)-ethoxyimino}-acetamido]-ceph-3-eme-4-carboxylic acid and 2.1 ml of 1-bromoethyl acetate were reacted to obtain 1.76 g of syn isomer of 1-(1-oxoethoxy)-ethyl 3-ethoxymethyl-7-[2-(2-amino-4-thiazolyl)-2-hydroxyimino-acetamido]-ceph-3-eme-4-carboxylate.

UV Spectrum (ethanol): Inflex. towards 220 nm $E_1^1=268$; Max. at 264 nm $E_1^1=369$; $\epsilon=18,900$.

UV Spectrum (0.1N HCl-ethanol): Inflex. towards 219 nm $E_1^1=286$; Max. at 261 nm $E_1^1=390$; $\epsilon-19,500$.

NMR Spectrum (DMSO): Peaks at 1-1.12-1.23 ppm ($CH_3$ of ethoxy); at 1.45-1.53 ppm (hydrogens of $CH_3$—CH); at 2.06 ppm (OAc); at 6.73 ppm (5-hydrogen of thiazole).

EXAMPLE 41

Syn isomer of 1-methoxycarbonyloxy-ethyl 3-methylthiomethyl-7-[2-(2-amino-4-thiazolyl)-2-hydroxyimino-acetamido]-ceph-3-eme-4-carboxylate

STEP A: Iodomethyl methylcarbonate

Chlorine was bubbled through 200 ml of ethyl chloroformate for 8 hours and the flask was hermetically sealed. The mixture stood at room temperature for 5 days and was then distilled at 50 mm Hg to recover the fraction boiling at 42° to 46° C. which was 1-chloroethyl chloroformate. 5 ml of the said product and 16 ml of methanol were stirred under an inert atmosphere at room temperature for one hour to obtain a solution containing chloromethyl methylcarbonate. The mixture was added to 38 ml of acetone and 10.9 g of sodium iodide were added thereto. The mixture was refluxed for 5 minutes and then returned to room temperature. The mixture was evaporated to dryness under reduced pressure at less than 40° C. and the residue was added to a mixture of 100 ml of ether and 75 ml of water. The decanted aqueous phase was extracted with ether and the organic phases were washed with water and with aqueous 0.25M sodium bisulfite solution, then with water and aqueous saturated sodium chloride solution, dried and evaporated to dryness under reduced pressure at no more than 40° C. to obtain iodoethyl methylcarbonate which was immediately used in the next step.

STEP B: Syn isomer of 1-methoxycarbonyloxy-ethyl 3-methylthiomethyl-7-[2-(2-amino-4-thiazolyl)-2-hydroxyimino-acetamido]-ceph-3-eme-4-carboxylate Using the procedure of Example 19, 3.2 g of the product of Step A and 3.72 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid were reacted to obtain 1.12 g of pure syn isomer of 1-methoxycarbonyloxy-ethyl 3-methylthiomethyl-7-[2-(2-amino-4-thiazolyl)-2-hydroxyimino-acetamido]-ceph-3-eme-4-carboxylate.

UV Spectrum (0.1N HCl-ethanol): Max. at 265 nm $E_1^1=365$; $\epsilon=19,400$.

NMR Spectrum (deuterochloroform): Peaks at 1.53-1.63 ppm (hydrogens of $CH_3$—CH); at 2.06 ppm (S—$CH_3$); at 3.83 ppm (—$COOCH_3$); at 7.05 ppm (5-hydrogen of thiazole); at 6.75 to 7.16 ppm (hydrogen of —CH—$CH_3$).

EXAMPLE 42

Syn isomer of 1-ethoxycarbonyloxy-ethyl 3-methylthiomethyl-7-[2-(2-amino-4-thiazolyl)-2-hydroxyimino-acetamido]-ceph-3-eme-4-carboxylate Using the procedure of Example 19, the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid and iodomethyl ethylcarbonate prepared using a procedure similar to Step A of Example 41 were reacted to obtain syn isomer of 1-ethoxycarbonyloxy-ethyl 3-methylthiomethyl-7-[2-(2-amino-4-thiazolyl)-2-hydroxyimino-acetamido]-ceph-3-eme-4-carboxylate.

NRM Spectrum (deuterochloroform): Peaks at 1.2 to 1.45 ppm ($CH_3$— of $COOCH_2$—$CH_3$); at 1.55-1.64 ppm (hydrogens of $CH_3$—CH—); at 6.9 ppm (5-hydrogen of thiazole); at 2.08 ppm (—$SCH_3$).

EXAMPLE 43

Syn isomer of methoxycarbonyloxymethyl 3-methylthiomethyl-7-[2-(2-amino-4-thiazolyl)-2-hydroxyimino-acetamido]-ceph-3-eme-4-carboxylate

STEP A: MONOIDO CARBONATE

Chlorine was bubbled for 5 hours through 30 ml of dimethylcarbonate heated to 65° C. under an inert atmosphere and the mixture was then allowed to stand for 56 hours. The mixture was distilled at 50 mm Hg to obtain 7.8 ml of monochlorocarbonate boiling at 59° to 61° C. A mixture of 5 ml of the said product, 7.8 g of sodium iodide and 30 ml of acetone was heated at 30° C. for 90 minutes and was then evaporated to dryness. The residue was added to a mixture of 100 ml of water and 100 ml of ether and the mixture was stirred for 5 minutes. The decanted aqueous phase was extracted with ether and the organic phase was washed with aqueous 0.25M sodium bisulfite solution, with water and with aqueous saturated sodium chloride solution, was dried and evaporated to dryness under reduced pressure at not more than 40° C. to obtain 7.93 g of monoiodocarbonate which was immediately used in the next step.

STEP B: Syn isomer of methoxycarbonyloxymethyl 3-methylthiomethyl-7-[2-(2-amino-4-thiazolyl)-2-hydroxyimino-acetamido]-ceph-3-eme-4-carboxylate Using the procedure of Example 19, 7.93 g of the product of Step A and 5 g of the syn isomer of 3-methylthiomethyl-7-[2-(2-tritylamino-4- thiazolyl)-2-{(1-methyl-1-methoxy)-ethoxyimino}-acetamido]-ceph-3-eme-4-carboxylic acid were reacted to obtain 0.537 g of pure syn isomer of methoxycarbonylmethyl 3-methylthiomethyl-7-[2-(2-amino-4-thiazolyl)-2-hydroxyimino-acetamido]-ceph-3-eme-4-carboxylate.

UV Spectrum (0.1N HCl-ethanol): Max. at 265 nm $E_1^1=371$; $\epsilon=19,200$.

NMR Spectrum (deuterochloroform): Peaks at 2.03 ppm ($SCH_3$); at 3.85 ppm ($COOCH_3$); at 6.96 ppm (5-hydrogen of thiazole); at 5.91 ppm ($COOCH_2$).

EXAMPLE 44

Syn isomer of 3-methylthiomethyl-7-[2-(2-amino-4-thiazolyl)-2-carboxymethoxyimino-acetamido]-ceph-3-eme-4-carboxylic acid

STEP A: Syn isomer of triethylamine 3-methylthiomethyl-7-[2-(2-tritylamino-4-thiazolyl)-2-hydroxyimino-acetamido]-ceph-3-eme-4-carboxylate A solution of 14.88 g of the syn isomer of 3-methylthiomethyl-7-[2-(2-tritylamino-4-thiazolyl)-2-{(1-methyl-1-methoxy)-ethoxyimino}-acetamido]-ceph-3-eme-4-carboxylic acid, 20 ml of 2N hydrochloric acid and 60 ml of acetone was stirred for 70 minutes at room temperature and the acetone was distilled. The mixture was diluted with 100 ml of water and was vacuum filtered and the product was washed with water and added to a mixture of 60 ml of acetone and 6 ml of water. 2.8 ml of triethylamine were added to the mixture and crystallization was induced. 20 ml of acetone were added which caused efflorescence and the mixture was vacuum filtered. The product was empasted with water and then with ether to obtain a first yield of 11.4 g of syn isomer of triethylamine 3-methylthiomethyl-7-[2-(2-tritylamino-4-thiazolyl)-2-hydroxyimino-acetamido]-ceph-3-eme-4-carboxylate. Then, after the residue was taken up in acetone, another 0.85 g of product was obtained for a total yield of 12.25 g.

NMR Spectrum (DMSO): Peaks at 1.96 ppm (hydrogens of $CH_3S$—); at 6.66 ppm (5-hydrogen of thiazole); at 7.36 ppm (trityl protons).

STEP B: Syn isomer of triethylamine 3-methylthiomethyl-7-[2-(2-tritylamino-4-thiazolyl)-2-(1,1-dimethylethoxycarbonyl-methoxyimino)-acetamido]-ceph-3-eme-4-carboxylate A mixture of 3.09 g of the product of Step A, 30 ml of demineralized water and 60 ml of methylene chloride was admixed at 20° C. with 5 ml of triethylamine and 4.8 g of tert.-butyl bromoacetate and the mixture was stirred at 20°-25° C. for 2½ hours. The mixture was acidified by addition of 10 ml of 2N hydrochloric acid and the decanted organic phase was washed twice with 100 ml of water. The wash waters were reextracted twice with 20 ml of methylene chloride and the combined organic phases were dried and filtered. The filtrate was evaporated to dryness under reduced pressure and the residue was empasted with ether and the mixture was vacuum filtered. The product was rinsed with ether and dried at 20° C. under reduced pressure to obtain 3 g of the acid. The latter was taken up in a mixture of 7.5 ml of benzene and 0.7 ml of triethylamine and 75 ml of ether were added to the resulting solution. The mixture was vacuum filtered and the product was rinsed 3 times with 2 ml of ether and dried to obtain 2.4 g of syn isomer of triethylamine 3-methylthiomethyl-7-[2-(2-tritylamino-4-thiazolyl)-2-(1,1-dimethylethoxycarbonylmethoxyimino)-acetamido]-ceph-3-eme-4-carboxylate which was used as for the next step.

NMR Spectrum (deuterochloroform): Peaks at 2.04 ppm (hydrogens of $CH_3S$—); at 4.76 ppm (hydrogens of =N—O—$CH_2$—); at 6.9 ppm (5-hydrogen of thiazole); at 7.36 ppm (trityl protons).

STEP C: Syn isomer of 3-methylthiomethyl-7-[2-(2-amino-4-thiazolyl)-2-carboxymethoxyimino-acetamido]-ceph-3-eme-4-carboxylic acid A mixture of 2.3 g of the product in Step B and 11.5 ml of trifluoroacetic acid was stirred for 25 minutes at 20° C. and the mixture was distilled in a water bath until the majority of the trifluoroacetic acid was gone. 100 ml of isopropyl ether were added to the mixture with cooling and the mixture was stirred at 20° C. for 30 minutes and was then vacuum filtered. The product was rinsed with isopropyl ether and dried to obtain 1.957 g of raw product which was dissolved in a mixture of 5 ml of an aqueous 1M sodium bicarbonate solution and 0.3 ml of triethylamine. 5 ml of aqueous saturated sodium chloride solution were added thereto and the mixture was chromatographed over silica gel. Elution was with aqueous 2M sodium chloride solution containing 4°/₀₀ of 1M sodium bicarbonate solution and the pH thereof was adjusted to 4 by addition of 50% aqueous formic acid. The resulting product was washed and dried to obtain 0.376 n of syn isomer of 3-methylthiomethyl-7-[2-(2-amino-4-thiazolyl)-2-carboxymethoxyimino-acetamido]-ceph-3-eme-4-carboxylic acid.

Analysis: $C_{16}H_{17}O_7N_5S_3$: molecular weight=487.534;Calculated: %C 39.42; %H 3.51; %N 14.36; %S 19.73; Found: %C 39.6; %H 3.7; %N 14.2; %S 18.7.

NMR Spectrum (DMSO): Peaks at 2 ppm (CH$_3$—S—); at 4.63 ppm (hydrogens of N—O—CH$_2$—); at 6.85 ppm (5-hydrogen of thiazole).

EXAMPLE 45

Syn isomer of 3-methylthiomethyl-7-[2-(2-amino-4-thiazolyl)-2-ethoxycarbonyloxyimino-acetamido]-ceph-3-eme-4-carboxylic acid STEP A: Syn isomer of triethylamine 3-methylthiomethyl-7-[2-(2-tritylamino-4-thiazolyl)-2-ethoxycarbonyloxyimino-aceteamido]-ceph-3-eme-4-carboxylate.

0.6 ml of ethyl chloroformate were added over 3 minutes at room temperature to a mixture of 2.32 g of the triethylamino salt of Step A of Example 44, 23 ml of dry methylene chloride and 0.5 ml of pyridine and after the mixture stood at room temperature for 15 minutes, 25 ml of water containing 6 ml of N hydrochloric acid were added thereto. The decanted aqueous phase was rinsed with 5 ml of methylene chloride and the combined organic phases were dried and vacuum filtered. The filter was rinsed with methylene chloride and the filtrate was evaporated to dryness. The residue was taken up in 20 ml of ethyl acetate and the mixture was stirred until total dissolution occured. 0.5 ml of triethylamine were added to the mixture and the mixture was vacuum filtered. The product was rinsed with ethyl acetate and ether and was dried to obtain 1.49 g of syn isomer of triethylamine 3-methylthiomethyl-7-[2-tritylamino-4-thiazolyl)-2-ethoxycarbonyloxyimino-acetamido]-ceph-3-eme-4-carboxylate.

STEP B: Syn isomer of 3-methylthiomethyl-7-[2-(2-amino-4-thiazolyl)-2-ethoxycarbonyloxyimino-acetamido]-ceph-3-eme-4-carboxylic acid The product of Step A was added to 7.6 ml of 67% aqueous formic acid and the mixture was stirred at 45° C. for 10 minutes and was vacuum filtered. The product was rinsed with 67% aqueous formic acid and to obtain 0.434 g of product. The filtrate was evaporated to dryness under reduced pressure at 35° C. and the residue was taken up in water and efflorescence occured. The mixture was vacuum filtered and the product was rinsed with water and was combined with 0.319 g of raw product produced in the same way. The product was dissolved in an aqueous 0.5M sodium bicarbonate solution and was chromatographed over silica gel. The product was eluted with aqueous 3M sodium chloride solution containing 4°/$_{oo}$ of sodium bicarbonate solution and the fraction with the desired product was adjusted to a pH of 3 by addition of acetic acid. The mixture stood at room temperature for 30 minutes and was vacuum filtered. The product was empasted 4 times with water and dried under reduced pressure to obtain 0.708 g of syn isomer of 3-methylthiomethyl-7-[2-(2-amino-4-thiazolyl)-2-ethoxycarbonyloxyimino-acetamido]-ceph-3-eme-4-carboxylic acid.

Analysis: C$_{17}$H$_{19}$O$_7$N$_5$S$_3$; molecular weight=501.56-;Calculated: %C 40.7; %H 3.8; %N 14.0; %S 19.2; Found: %C 40.7; %H 3.7; %N 13.9; %S 19.3;

NMR Spectrum (DMSO): Peaks at 1.26 ppm (t: J=7 Hz) (hydrogens of COOCH$_2$—CH$_3$); at 2 ppm (hydrogens of CH$_3$—S—); at 4.25 ppm (q: J=7 Hz) (hydrogens of COOCH$_2$—CH$_3$); at 7.11 ppm (5-hydrogen of thiazole.)

EXAMPLE 46

Injectable preparations were prepared containing 500 mg of either the syn isomer of 3-methoxymethyl-7-[2-(2-amino-4-thiazolyl)-2-hydroxyimino-acetamido]-ceph-3-eme-4-carboxylic acid or the syn isomer of 3-methylthiomethyl-7-[2-(2-amino-4-thiazolyl)-2-methoxyimino-acetamido]-ceph-3-eme-4-carboxylic acid and sufficient sterile aqueous excipient for a final volume of 5 ml.

Gelules were prepared containing 250 mg of either the syn isomer of (1-oxopropoxy)-methyl 3-methoxymethyl-7-[2-(2-amino-4-thiazolyl)-2-hydroxyiminoacetamido]-ceph-3-eme-4-carboxylate or the syn isomer of (1-oxopropoxy)-methyl 3-methylthiomethyl-7-[2-(2-amino-4-thiazolyl)-2-hydroxyiminoacetamido]-ceph-3-eme-4-carboxylate or the syn isomer of 1-(acetyloxy)-ethyl 3-methylthiomethyl-7-[2-(2-amino-4-thiazolyl)-2-hydroxyimino-acetamido]-ceph-3-eme-4-carboxylate or the syn isomer of 1-(methoxycarbonyloxy)-ethyl 3-methylthiomethyl-7-[2-(2-amino-4-thiazolyl)-2-hydroxyimino-acetamido]-ceph-3-eme-4-carboxylate or the syn isomer of 1-(ethoxycarbonyloxy)-ethyl 3-methylthiomethyl-7-[2-(2-amino-4-thiazolyl)-2-hydroxyimino-acetamido]-ceph-3-eme-4-carboxylate and sufficient excipient for a final gelule of 400 mg.

PHARMACOLOGICAL STUDY

A. In Vitro Activity

A series of tubes were prepared containing the same amounts of sterile nutritive medium and each tube then received increasing amounts of the test compounds after which each tube was seeded with a bacterial strain. After incubation for 24 or 48 hours in an oven at 37° C., the inhibition was determined by transillumination to determine the minimum inhibitory concentration (M.P.C.) expressed in mg/ml. The results are shown in the following Table.

| | PRODUCT OF EXAMPLE 1 | |
|---|---|---|
| | M.I.C. in μg/ml | |
| STRAINS | 24 h | 48 h |
| *Staphylococcus aureus* ATCC 6 538 Penicillin Sensitive | 1 | 1 |
| *Staphylococcus aureus* UC 1 128 Penicillin Resistant | 0,5 | 1 |
| *Staphylococcus aureus* exp. n° 54 146 | 0,5 | 2 |
| *Streptococcus pyogenes* A 561 | 0,2 | 0,2 |
| *Streptococcus faecalis* 5 432 | 10 | 10 |
| *Streptococcus faecalis* 99 F 74 | 10 | 20 |
| *Bacillus subtilis* ATCC 6 633 | 1 | 2 |
| *Escherichia Coli* Sensible Tétracycline ATCC 9 637 | 1 | 1 |
| *Escherichia Coli* Resistant Tétracycline ATCC 11 303 | 0,5 | 0,5 |
| *Escherichia Coli* Exp. TO$_{26}$B$_6$ | 0,5 | 1 |
| *Escherichia Coli* Resistant Gentamicine Tobramycine R 55 123 D | 1 | 1 |
| *Klebsiella pneumoniae* Exp. 52 145 | 0,2 | 0,5 |
| *Klebsiella pneumoniae* 2 536 Resistant Gentamycine | 0,5 | 1 |
| *Proteus mirabilis* (indol−) A 235 | 0,3 | 0,5 |
| *Salmonella typhimurium* 420 | 0,5 | 1 |

| PRODUCT OF EXAMPLE 2 | | |
|---|---|---|
| | M.I.C. in μg/ml | |
| STRAINS | 24 h | 48 h |
| *Staphylococcus aureus* ATCC 6 538 Penicillin Sensitive | 3 | 5 |
| *Staphylococcus aureus* UC 1 128 Penicillin Resistant | 5 | 10 |
| *Staphylococcus aureus* exp. n° 54 146 | 3 | 5 |
| *Streptococcus pyogenes* A 561 | 0,3 | 0,5 |
| *Bacillus subtilis* ATCC 6 633 | 10 | 20 |
| *Escherichia Coli* Sensible Tétracycline ATCC 9 637 | 20 | 20 |
| *Escherichia Coli* Resistant Tétracycline ATCC 11 303 | 3 | 3 |
| *Escherichia Coli* Exp. TO$_{26}$B$_6$ | 2 | 3 |
| *Escherichia Coli* Resistant Gentamicine Tobramycine R 55 123 D | 5 | 10 |
| *Klebsiella pneumoniae* Exp. 52 145 | 3 | 3 |
| *Klebsiella pneumoniae* 2 536 Resistant Gentamycine | 20 | 20 |
| *Proteus mirabilis* (indol−) A 235 | 3 | 3 |
| *Salmonella typhimurium* 420 | 5 | 5 |

| PRODUCT OF EXAMPLE 3 | | |
|---|---|---|
| | M.I.C. in μg/ml | |
| STRAINS | 24 h | 48 h |
| *Staphylococcus aureus* ATCC 6 538 Penicillin Sensitive | 1 | 2 |
| *Staphylococcus aureus* UC 1 128 Penicillin Resistant | 3 | 3 |
| *Staphylococcus aureus* exp. n° 54 146 | 2 | 2 |
| *Streptococcus pyogenes* A 561 | ≦0,02 | ≦0,02 |
| *Streptococcus faecalis* 5 432 | 20 | 40 |
| *Streptococcus faecalis* 99 F 74 | 20 | >40 |
| *Bacillus subtilis* ATCC 6 633 | 1 | 3 |
| *Escherichia Coli* Sensible Tétracycline ATCC 9 637 | 1 | 1 |
| *Escherichia Coli* Resistant Tétracycline ATCC 11 303 | 0,1 | 0,1 |
| *Escherichia Coli* Exp. TO$_{26}$B$_6$ | 0,2 | 0,2 |
| *Escherichia Coli* Resistant Gentamicine Tobramycine R 55 123 D | 0,5 | 0,5 |
| *Klebsiella pneumoniae* Exp. 52 145 | 0,05 | 0,1 |
| *Klebsiella pneumoniae* 2 536 Resistant Gentamycine | 0,5 | 0,5 |
| *Proteus mirabilis* (indol−) A 235 | 0,05 | 0,05 |
| *Salmonella typhimurium* 420 | 0,5 | 0,5 |
| *Providencia* DU 48 | 5 | 5 |
| *Serratia* Resistant Gentamicine 2 532 | 2 | 2 |

| PRODUCT OF EXAMPLE 4 | | |
|---|---|---|
| | M.I.C. in μg/ml | |
| STRAINS | 24 h | 48 h |
| *Staphylococcus aureus* ATCC 6 538 Penicillin Sensitive | 0,2 | 0,5 |
| *Staphylococcus aureus* UC 1 128 Penicillin Resistant | 0,5 | 0,5 |
| *Staphylococcus aureus* exp. n° 54 146 | 0,2 | 0,5 |
| *Streptococcus pyogènes* A 561 | ≦0,02 | ≦0,02 |
| *Streptococcus* faecalis 5 432 | 5 | 10 |
| *Streptococcus* faecalis 99 F 74 | 3 | 10 |
| *Bacillus subtilis* ATCC 6 633 | 0,5 | 1 |
| *Escherichia Coli* Sensible Tétracycline ATCC 9 637 | 2 | 3 |
| *Escherichia Coli* Resistant Tétracycline ATCC 11 303 | 0,2 | 0,5 |
| *Escherichia Coli* Exp. TO$_{26}$B$_6$ | 0,5 | 0,5 |
| *Escherichia Coli* Resistant Gentamicine Tobramycine R 55 123 D | 1 | 1 |
| *Klebsiella pneumoniae* Exp. 52 145 | 0,2 | 0,2 |

-continued

| PRODUCT OF EXAMPLE 4 | | |
|---|---|---|
| | M.I.C. in μg/ml | |
| STRAINS | 24 h | 48 h |
| *Klebsiella pneumoniae* 2 536 Resistant Gentamycine | 2 | 3 |
| *Proteus mirabilis* (indol−) A 235 | 0,5 | 1 |
| *Salmonella typhimurium* 420 | 1 | 1 |

| PRODUCT OF EXAMPLE 6 | | |
|---|---|---|
| | M.I.C. in μg/ml | |
| STRAINS | 24 h | 48 h |
| *Staphylococcus aureus* ATCC 6 538 Penicillin Sensitive | 1 | 2 |
| *Staphylococcus aureus* UC 1 128 Penicillin Resistant | 2 | 2 |
| *Staphylococcus aureus* exp. n° 54 146 | 2 | 2 |
| *Streptococcus pyogenes* A 561 | 0,05 | 0,05 |
| *Streptococcus faecalis* 5 432 | 1 | >40 |
| *Streptococcus faecalis* 99 F 74 | 2 | >40 |
| *Bacillis subtilis* ATCC 6 633 | 1 | 2 |
| *Escherichia Coli* Sensible Tétracycline ATCC 9 637 | 3 | 3 |
| *Escherichia Coli* Resistant Tétracycline ATCC 11 303 | 0,5 | 0,5 |
| *Escherichia Coli* Exp. TO$_{26}$B$_6$ | 1 | 1 |
| *Escherichia Coli* Resistant Gentamicine Tobramycine R 55 123 D | 1 | 1 |
| *Klebsiella pneumoniae* Exp. 52 145 | 0,1 | 0,1 |
| *Klebsiella pneumoniae* 2 536 Resistant Gentamycine | 2 | 2 |
| *Proteus mirabilis* (indol−) A 235 | 0,2 | 0,2 |
| *Salmonella typhimurium* 420 | 1 | 2 |
| *Serratia* Resistant Gentamicine 2 532 | 2 | 3 |

| PRODUCT OF EXAMPLE 7 | | |
|---|---|---|
| | M.I.C. in μg/ml | |
| STRAINS | 24 H | 48 H |
| *Staphylococcus aureus* ATCT 6 538 Penicillin Sensitive | 0,2 | 0,5 |
| *Staphylococcus aureus* UC 1 128 Penicillin Resistant | 0,5 | 0,5 |
| *Staphylococcus aureus* exp. n° 54 146 | 0,2 | 0,5 |
| *Streptococcus pyogenes* A 561 | ≦0,02 | ≦0,02 |
| *Streptococcus faecalis* 5 432 | 10 | 20 |
| *Streptococcus faecalis* 99 F 74 | 3 | 20 |
| *Escherichia Coli* Sensible Tétracycline 7624 | 3 | 3 |
| *Escherichia Coli* Resistant Tétracycline ATCC 11 303 | 1 | 1 |
| *Escherichia Coli* Exp. TO$_{26}$B$_6$ | 2 | 2 |
| *Escherichia Coli* Resistant Gentamicine, Tobramycine R 55 123 D | 5 | 5 |
| *Klebsiella pneumoniae* Exp. 52 145 | 1 | 1 |
| *Klebsiella pneumoniae* 2 536 Resistant Gentamycine | 10 | 10 |
| *Proteus mirabilis* (indol+) A 235 | 1 | 2 |
| *Salmonella typhimurium* 420 | 5 | 5 |

| PRODUCT OF EXAMPLE 8 | | |
|---|---|---|
| | M.I.C. in μg/ml | |
| STRAINS | 24 H | 48 H |
| *Staphylococcus aureus* ATCT 6 538 Penicillin Sensitive | 0,5 | 0,5 |
| *Staphylococcus aureus* UC 1 128 Penicillin Resistant | 1 | 1 |

PRODUCT OF EXAMPLE 8

| STRAINS | M.I.C. in µg/ml | |
|---|---|---|
| | 24 H | 48 H |
| *Staphylococcus aureus* exp. n° 54 146 | 0,5 | 1 |
| *Streptococcus pyrogenes A 561* | 0,05 | 0,05 |
| *Streptococcus faecalis 5 432* | 5 | 10 |
| *Streptococcus faecalis 99 F 74* | 2 | 10 |
| *Escherichia Coli* Sensible Tétracycline 7624 | 1 | 1 |
| *Escherichia Coli* Resistant Tétracycline ATCC 11 303 | 0,5 | 0,5 |
| *Escherichia Coli* Exp. TO$_{26}$B$_6$ | 0,5 | 1 |
| *Escherichia Coli* Resistant Gentamicine, Tobramycine R 55 123 D | 1 | 1 |
| *Klebsiella pneumoniae* Exp. 52 145 | 0,5 | 0,5 |
| *Klebsiella pneumoniae* 2 536 Resistant Gentamycine | 2 | 3 |
| *Proteus mirabilis* (indol−) A 235 | 0,5 | 1 |
| *Salmonella typhimurium 420* | 1 | 1 |

PRODUCT OF EXAMPLE 17

| STRAINS | M.I.C. in µg/ml | |
|---|---|---|
| | 24 H | 48 H |
| *Staphylococcus aureus* ATCT 6 538 Penicillin Sensitive | 0,5 | 0,5 |
| *Staphylococcus aureus* UC 1 128 Penicillin Resistant | 0,5 | 0,5 |
| *Staphylococcus aureus* exp. n° 54 146 | 1 | 1 |
| *Streptococcus pyrogenes A 561* | ≦0,02 | ≦0,02 |
| *Escherichia Coli* Sensible Tétracycline 7624 | 3 | 5 |
| *Escherichia Coli* Resistant Tétracycline ATCC 11 303 | 3 | 5 |
| *Escherichia Coli* Exp. TO$_{26}$B$_6$ | 2 | 2 |
| *Escherichia Coli* Resistant Gentamicine, Tobramycine R 55 123 D | 3 | 3 |
| *Klebsiella pneumoniae* Exp. 52 145 | 0,5 | 1 |
| *Klebsiella pneumoniae* 2 536 Resistant Gentamycine | 10 | 10 |
| *Proteus mirabilis* (indol−) A 235 | 1 | 2 |
| *Salmonella typhimurium 420* | 1 | 5 |

PRODUCT OF EXAMPLE 18

| STRAINS | M.I.C. in µg/ml | |
|---|---|---|
| | 24 H | 48 H |
| *Staphylococcus aureus* ATCT 6 538 Penicillin Sensitive | 0,5 | 0,5 |
| *Staphylococcus aureus* UC 1 128 Penicillin Resistant | 1 | 2 |
| *Staphylococcus aureus* exp. n° 54 146 | 1 | 1,5 |
| *Streptococcus pyrogenes A 561* | ≦0,02 | ≦0,02 |
| *Escherichia Coli* Sensible Tétracycline 7624 | 3 | 5 |
| *Escherichia Coli* Resistant Tétracycline ATCC 11 303 | 1 | 2 |
| *Escherichia Coli* Exp. TO$_{26}$B$_6$ | 3 | 3 |
| *Escherichia Coli* Resistant Gentamicine, Tobramycine R 55 123 D | 2 | 2 |
| *Klebsiella pneumoniae* Exp. 52 145 | 0,5 | 0,5 |
| *Klebsiella pneumoniae* 2 536 Resistant Gentamycine | 10 | 10 |
| *Proteus mirabilis* (indol−) A 235 | 1 | 2 |
| *Salmonella typhimurium 420* | 3 | 5 |

PRODUCT OF EXAMPLE 44

| STRAINS | M.I.C. in µg/ml | |
|---|---|---|
| | 24 H | 48 H |
| *Staphylococcus aureus* ATCT 6 538 Penicillin Sensitive | 3 | 5 |
| *Staphylococcus aureus* UC 1 128 Penicillin Resistant | 5 | 5 |
| *Staphylococcus aureus* exp. n° 54 146 | 5 | 10 |
| *Streptococcus pyrogenes A 561* | 0,2 | 0,2 |
| *Escherichia Coli* Sensible Tétracycline 7624 | 1 | 2 |
| *Escherichia Coli* Resistant Tétracycline ATCC 11 303 | 0,2 | 0,5 |
| *Escherichia Coli* Exp. TO$_{26}$B$_6$ | 0,5 | 0,5 |
| *Escherichia Coli* Resistant Gentamicine, Tobramycine R 55 123 D | 2 | 2 |
| *Klebsiella pneumoniae* Exp. 52 145 | 0,2 | 0,5 |
| *Klebsiella pneumoniae* 2 536 Resistant Gentamycine | 1 | 1 |
| *Proteus mirabilis* (indol−) A 235 | 0,05 | 0,1 |
| *Proteus vulgaris* (indol+) A 232 | 0,1 | 0,1 |
| *Salmonella typhimurium 420* | | |
| PROVIDENCIA DU 48 | 1 | 5 |
| SERRATIA RESISTANT GENTAMICINE 2 532 | 1 | 1 |

PRODUCT OF EXAMPLE 45

| STRAINS | M.I.C. in µg/ml | |
|---|---|---|
| | 24 H | 48 H |
| *Staphylococcus aureus* ATCT 6 538 Penicillin Sensitive | 0,5 | 0,5 |
| *Staphylococcus aureus* UC 1 128 Penicillin Resistant | 1 | 1 |
| *Staphylococcus aureus* exp. n° 54 146 | 0,5 | 1 |
| *Streptococcus pyrogenes A 561* | ≦0,02 | ≦0,02 |
| *Streptococcus faecalis 5 432* | 10 | 10 |
| *Streptococcus faecalis 99 F 74* | 3 | 10 |
| *Escherichia Coli* Sensible Tétracycline 7624 | 1 | 2 |
| *Escherichia Coli* Resistant Tétracycline ATCC 11 303 | 0,5 | 0,5 |
| *Escherichia Coli* Exp. TO$_{26}$B$_6$ | 1 | 1 |
| *Escherichia Coli* Resistant Gentamicine, Tobramycine R 55 123 D | 1 | 1 |
| *Klebsiella pneumoniae* Exp. 52 145 | 0,2 | 0,5 |
| *Klebsiella pneumoniae* 2 536 Resistant Gentamycine | 3 | 3 |
| *Proteus mirabilis* (indol−) A 235 | 0,5 | 1 |
| *Salmonella typhimurium 420* | 2 | 2 |
| SERRATIA RESISTANT GENTAMICINE 2 532 | 3 | 5 |

In the following Table, the strains used were as follows:

| Strain A | *Staphylococcus aureus* ATCC 6 538 Penicillin Sensitive |
|---|---|
| Strain B | *Staphylococcus aureus* UC 1 128 Penicillin Resistance |
| Strain C | *Staphylococcus aureus* exp. n° 54 146 |
| Strain D | *Streptococcus pyogenes* A 561 |
| Strain E | *Bacillus subtilis* ATCC 6 633 |
| Strain F | *Escherichia Coli* Resistant Tétracycline ATCC 11 303 |
| Strain G | *Escherichia Coli* Exp. T026B6 |
| Strain H | *Escherichia Coli* Resistant Gentamicine Tobramycine R 55 123 D |
| Strain I | *Klebsiella pneumoniae* Exp. 52 145 |
| Strain J | *Klebsiella pneumoniae* 2 536 Resistant Gentamycine |
| Strain K | *Proteus mirabilis* (Indol−) A 235 |
| Strain L | *Proteus vulgaris* A 232 |
| Strain M | *Salmonella typhimurium* 420 |

The results in the following Table are expressed in mice after 24 hours of incubation.

| STRAINS | A | B | C | D | E | F | G | H | I | J | K | L | M |
|---|---|---|---|---|---|---|---|---|---|---|---|---|---|
| Product of Example | | | | | | | | | | | | | |
| 9 | 2 | 2 | 2 | ≦0,02 | 3 | 1 | 1 | 2 | 0,5 | 3 | 0,2 | 10 | 2 |
| 10 | 1 | 2 | 1 | ≦0,02 | 2 | 0,5 | 1 | 1 | 1 | 3 | 0,5 | 2 | 2 |
| 11 | 2 | 3 | 2 | ≦0,02 | 2 | 0,5 | 1 | 1 | 1 | 3 | 0,5 | 2 | 2 |
| 12 | 2 | 3 | 2 | 0,05 | 5 | 1 | 3 | 3 | 1 | 5 | 1 | 5 | 3 |
| 13 | 1 | 2 | 1 | ≦0,02 | 1 | 2 | 5 | 5 | 2 | 10 | 1 | — | 3 |
| 14 | 3 | 10 | 3 | 0,05 | 2 | 0,5 | 1 | 1 | 0,2 | 3 | 0,2 | 2 | 2 |

B. In Vivo Antibiotic Activity

Groups of 10 male mice of Charles River CDI strain weighing about 21 to 22 g were interperitoneally infected with 0.5 ml of a 22 hour culture of a strain of Staphylococcus aureus No. 54, 146 (antibiotic medium 3 with a pH of 7) diluted 1/6 with physiological water. The products were orally administered at different doses in 0.5 ml of distilled water by intubation one, 5 and 24 hours after the injection. The number of mice surviving after 10 days were determined and the results are reported in the following Table.

| Product of Example | Oral dose in mg | No. of mice living on 10th day |
|---|---|---|
| 5 | 0,1 | 2 |
|  | 0,25 | 9 |
|  | 0,5 | 10 |
| 22 | 0,1 | 9 |
|  | 0,25 | 10 |
|  | 0,5 | 10 |
| 28 | 0,1 | 1 |
|  | 0,25 | 7 |
|  | 0,5 | 9 |
| 29 | 0,1 | 0 |
|  | 0,25 | 5 |
|  | 0,5 | 9 |
| 30 | 0,1 | 0 |
|  | 0,25 | 7 |
|  | 0,5 | 10 |

Various modifications of the products and processes of the invention may be made without departing from the spirit or scope thereof and it should be understood that the invention is intended to be limited only as defined in the appended claims.

What we claim is:

1. A syn isomer compound having a formula selected from the group consisting of

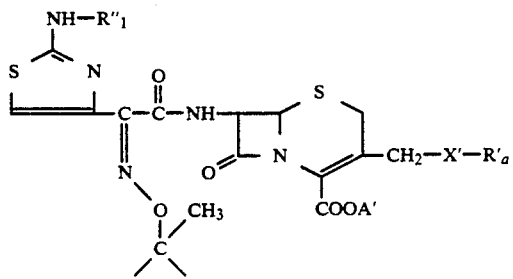

and

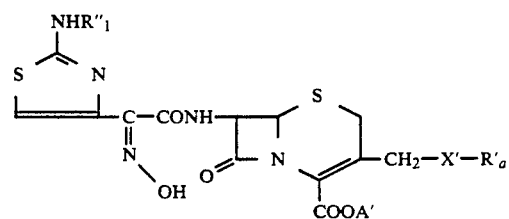

wherein A' is selected from the group consisting of hydrogen, alkali metal, alkaline earth metal, $-NH_4$, magnesium, non-toxic, pharmaceutically acceptable organic amine and an easily cleavable ester group $R'_2$ is selected from the group consisting of alkyl of 1 to 6 carbon atoms optionally interrupted with an oxygen atom, alkenyl and alkynyl of 2 to 6 carbon atoms and aralkyl of 7 to 12 carbon atoms optionally substituted with at least one member of the group consisting of carboxy, amino, aminoalkyl of 1 to 6 carbon atoms, alkyl of 1 to 6 carbon atoms, dialkylamino of 1 to 6 carbon atoms and dialkylaminoalkyl of 1 to 6 carbon atoms, $X^1$ is selected from the group consisting of oxygen and sulfur optionally oxidized to sulfoxide or sulfone and $R_1''$ is an amino protective group.

* * * * *